(12) United States Patent
Spector et al.

(10) Patent No.: US 7,829,297 B2
(45) Date of Patent: Nov. 9, 2010

(54) TREATMENT OF CANCERS EXPRESSING P95 ERBB2

(75) Inventors: Neil Lee Spector, Durham, NC (US); Wenle Xia, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 12/366,457

(22) Filed: Feb. 5, 2009

(65) Prior Publication Data

US 2009/0192189 A1 Jul. 30, 2009

Related U.S. Application Data

(63) Continuation of application No. 10/567,012, filed as application No. PCT/US2004/024888 on Aug. 2, 2004, now abandoned.

(60) Provisional application No. 60/491,752, filed on Aug. 1, 2003.

(51) Int. Cl.
| | |
|---|---|
| A61K 38/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |
| A01N 37/18 | (2006.01) |

(52) U.S. Cl. ............................ 435/7.1; 435/4; 514/2; 530/300; 530/350

(58) Field of Classification Search .............. 435/4, 435/7.1; 514/2; 530/300, 350
See application file for complete search history.

(56) References Cited

U.S. PATENT DOCUMENTS

| | | |
|---|---|---|
| 6,169,091 B1 | 1/2001 | Cockerill et al. |
| 6,174,889 B1 | 1/2001 | Cockerill et al. |
| 6,207,669 B1 | 3/2001 | Cockerill et al. |
| 6,391,874 B1 | 5/2002 | Cockerill et al. |
| 6,541,214 B1 | 4/2003 | Clinton |
| 2003/0219842 A1 | 11/2003 | Carney et al. |
| 2005/0272120 A1* | 12/2005 | Dowd et al. ................. 435/69.1 |
| 2006/0094068 A1* | 5/2006 | Bacus et al. ............... 435/7.23 |

FOREIGN PATENT DOCUMENTS

| | | |
|---|---|---|
| WO | 9935146 A1 | 7/1999 |
| WO | 0104111 A1 | 1/2001 |
| WO | 0202552 A1 | 1/2002 |
| WO | 02056912 A2 | 7/2002 |
| WO | 03086467 A1 | 10/2003 |

OTHER PUBLICATIONS

Chen et al.; "Strategies to Target HER2/neu Overexpression for Cancer Therapy"; Drug Resistance Updates; 2003; vol. 6, No. 3; pp. 129-136.
Molina et al.; "NH(2)-Terminal Truncated HER-2 Protein but not Full Length Receptor is Associated with Nodal Metastasis in Human Breast Cancer"; Clinical Cancer Research; 2002; vol. 8, No. 2; pp. 347-353.
Zhou et al.; "Effects of the EGFR/HER2 Kinase Inhibitor GW572016 on EGFR- and HER2-Overexpressing Breast Cancer Cell Line Proliferation, Radiosensitization and Resistance"; International Journal of Radiation: Oncology Biology Physics; 2004; vol. 58, No. 2; pp. 344-352.
Xia et al.; "Truncated ErbB2 Receptor (p95 ErbB2) is Regulated by Heregulin through Heterodimer Formation with ErbB3 Yet Remains Sensitive to the Dual EGFR/ErbB2 Kinase Inhibitor GW572016"; Oncogene; 2004; vol. 23, No. 3; pp. 646-653.
Harris et al.; "Comparison of Methods of Measuring HER-2 in Metastatic Breast Cancer Patients Treated with High-Dose Chemotherapy"; Journal of Clinical Oncology; 2001; vol. 19, No. 6; pp. 1698-1706.
Difiore et al.; "erbB2 is a Potent Oncogene when Overexpressed in NIH/3T3 Cells"; Science; 1987; vol. 237; pp. 178-182.
Rusnak et al.; "The Effects of the Novel, Reversible Epidermal Growth Factor Receptor/ErbB-2 Tyrosine Kinase Inhibitor, GW2016, on the Growth of Human Normal and Tumor-Derived Cell Lines in vitro and in vivo"; Molecular Cancer Therapeutics; 2001; vol. 1, No. 2; pp. 85-94.
Baselga et al.; "Phase II Study of Weekly Intravenous Recombinant Humanized Anti-p185(HER2) Monoclonal Antibody in Patients with HER2/neu-Overexpressing Metastatic Breast Cancer"; Journal of Clinical Oncology; 1996; vol. 14, No. 3; pp. 737-744.
Rusnak et al.; "The Characterization of Novel, Dual ErbB-2/EGFR, Tyrosine Kinase Inhibitors: Potential Therapy for Cancer"; Cancer Research; 2001; vol. 61, No. 19; pp. 7196-7203.
Colomer et al.; "Circulating HER2 Extracellular Domain and Resistance to Chemotherapy in Advanced Breast Cancer"; Clinical Cancer Research; 2000; vol. 6, No. 6; pp. 2356-2362.
Burris; "Dual Kinase Inhibition in the Treatment of Breast Cancer: Initial Experience with the EGFR/erbB-2 Inihbitor Lapatinib"; The Oncologist; 2004; vol. 9, Suppl. 3; pp. 10-15.

(Continued)

*Primary Examiner*—Alana M Harris
(74) *Attorney, Agent, or Firm*—J. Scott Young

(57) ABSTRACT

The truncated ErbB2 receptor ($p95^{ErbB2}$) is shown to differ from the full-length ErbB2 receptor in its association with other ErbB receptors. The truncated receptor preferentially associated with ErbB3, whereas full length ErbB2 heterodimerizes with either EGFR or ErbB3. Consistent with $p95^{ErbB2}$ heterodimerization with ErbB3, it is shown that heregulin (an ErbB3 ligand) stimulates $p95^{ErbB2}$ phosphorylation in breast cancer cell lines. Described herein are methods of identifying patients suitable for treatment with a $p95^{ErbB2}$ inhibitor, and methods of treating such patients.

8 Claims, 11 Drawing Sheets

OTHER PUBLICATIONS

Molina et al.; "Trastuzumab (Herceptin), a Humanized Anti-HER2 Receptor Monoclonal Antibody, Inhibits Basal and Activated HER2 Ectodomain Cleavage in Breast Cancer Cells"; Cancer Research; 2001; vol. 61, No. 12; pp. 4744-4749.

Bargmann et al.; "Oncogenic activiation of the neu-encoded receptor protein by point mutation and deletion"; The EMBO Journal; 1988; vol. 7, No. 7; pp. 2043-2052.

Segatto et al.; "Different Structural Alterations Upregulate in vitro Tyrosine Kinase Activity and Transforming Potency of the erbB-2 Gene"; Molecular and Cellular Biology; 1988; vol. 8, No. 12; pp. 5570-5574.

Christianson et al.; "NH2-Terminally Truncated HER-2/neu Protein: Relationship with Shedding of the Extracellular Domain and with Prognostic Factors in Breast Cancer"; Cancer Research; 1998; vol. 58, No. 22; pp. 5123-5129.

Xia et al.; "Anti-Tumor Activity of GW572016: a Dual Tyrosine Kinase Inhibitor Blocks EGF Activation of EGFR/erbB2 and Downstream Erk1/2 and AKT Pathways"; Oncogene; 2002; vol. 21, No. 41; pp. 6255-6263.

* cited by examiner

TREATMENT OF CANCERS EXPRESSING P95 ERBB2

CROSS-REFERENCE TO RELATED APPLICATIONS

This application is a continuation of U.S. application Ser. No. 10/567,012 filed Feb. 1, 2006; which was filed pursuant to 35 U.S.C. §371 as a U.S. National Phase Application of International Application No. PCT/US2004/024888 filed Aug. 2, 2004; which claims priority from U.S. Provisional Application No. 60/491,752 filed Aug. 1, 2003.

FIELD OF THE INVENTION

The present invention relates to methods of treating solid tumors that express $p95^{ErbB2}$, and methods for selecting subjects suitable for such treatment.

BACKGROUND

Many existing anti-cancer chemotherapeutics are non-specific, in that they typically damage or kill normal cells as well as malignant cells. Research in oncology is increasingly focused on targeted therapies, in which a therapeutic compound interacts with a specific molecule to interfere with a particular molecular pathway. Tumors in different individuals, even when found at the same anatomic location, can differ in their molecular signalling pathways. Accordingly, it is important to know which molecules and pathways are targeted by a therapeutic compound, so that the treatment can be provided to the appropriate patients. Determining which molecules and pathways are affected by a therapeutic compound also provides diagnostic techniques to identify those patients suitable for treatment with that therapeutic.

ErbB Receptors

The ErbB family of type I receptor tyrosine kinases includes ErbB1 (also known as the epidermal growth factor receptor (EGFR or HER1)), ErbB2 (also known as Her2), ErbB3, and ErbB4. These receptor tyrosine kinases are widely expressed in epithelial, mesenchymal, and neuronal tissues where they play a role in regulating cell proliferation, survival, and differentiation (Sibilia and Wagner, Science, 269: 234 (1995); Threadgill et al., Science, 269: 230 (1995)). Increased expression of wild-type ErbB2 or EGFR, or expression of constitutively activated receptor mutants, transforms cells in vitro (Di Fiore et al., 1987; DiMarco et al., Oncogene, 4: 831 (1989); Hudziak et al., Proc. Natl. Acad. Sci. USA., 84: 7159 (1987); Qian et al., Oncogene, 10: 211 (1995)). Increased expression of ErbB2 or EGFR has been correlated with a poorer clinical outcome in some breast cancers and a variety of other malignancies (Slamon et al., Science, 235: 177 (1987); Slamon et al., Science, 244: 707 (1989); Bacus et al, Am. J. Clin. Path., 102: S13 (1994)).

A family of peptide ligands binds to and activates ErbB receptor signaling, and includes epidermal growth factor (EGF) and transforming growth factor α (TGF-α), each of which binds to EGFR (Reise and Stem, Bioessays, 20: 41 (1998); Salomon et al., Crit. Rev. Oncol. Hematol., 19: 183 (1995)). Ligand-receptor interactions are selective in that epidermal growth factor (EGF) and transforming growth factor alpha (TGFα) bind EGFR while heregulin binds ErbB3 and ErbB4. Ligand binding induces ErbB receptor phosphorylation (activation) with subsequent formation of homo- and heterodimers. ErbB2 is the preferred heterodimeric partner for EGFR, ErbB3, and ErbB4 (Graus-Porta et al., EMBO J., 16: 1647 (1997); Tzahar et al., Mol. Cell. Biol., 16: 5276 (1996)). A number of soluble ligands have been identified for EGFR, ErbB3, and ErbB4, but none have been identified for ErbB2, which seems to be transactivated following heterodimerization (Ullrich and Schlessinger, Cell, 61: 203 (1990); Wada et al., Cell, 61: 1339 (1990); Karunagaran et al., EMBO J., 15: 254 (1996); Stem and Kamps, EMBO J., 7: 995 (1988)).

Truncated ErbB2

The ErbB2 gene encodes a Mr 185,000 member of the ErbB family. The full-length ErbB2 receptor ($p185^{ErbB2}$) undergoes proteolytic cleavage releasing its extracellular domain (ECD), which can be detected in cell culture medium and in patient's sera. (Lin and Clinton, Oncogene 6: 639 (1991); Zabrecky et al., J. Biol. Chem. 266: 1716 (1991); Pupa et al., Oncogene 8: 2917 (1993)). Cleavage of ErbB2 appears to be mediated by a member of the matrix metalloprotease (MMP) family (Codony-Servat et al., Cancer Res. 59: 1196 (1999)). The truncated ErbB2 receptor ($p95^{ErbB2}$) that remains after proteolytic cleavage exhibits increased autokinase activity and transforming efficiency compared with the full-length receptor, implicating the ErbB2 ECD as a negative regulator of ErbB2 kinase and oncogenic activity. (Di Fiore et al., Science 237: 178 (1987); Bargmann and Weinberg, EMBO J 7: 2043 (1988); Segatto et al., Mol. Cell. Biol. 8: 5570 (1988)).

Expression of the $p95^{ErbB2}$ truncated ErbB2 receptors in breast cancer cells has been correlated with positive lymph node metastasis in ErbB2 overexpressing tumors. (Christianson et al., Cancer Res. 58: 5123 (1998); Molina et al., Clin. Cancer Res. 8: 347 (2002)). Elevated serum levels of ErbB2 ECD in women with breast cancer has also been correlated with a poorer response to therapy. (Brandt-Rauf, Mutat. Research 333: 203 (1995); Kandl et al., Br. J. Cancer 70: 739 (1994); Yamauchi et al., J. Clin. Oncol. 15: 2518 (1996); Colomer et al., Clin. Cancer Research 6: 2356 (2000)).

Therapeutics and ErbB2

Trastuzumab (Herceptin™), a humanized anti-ErbB2 monoclonal antibody has been approved for the treatment of breast cancers that either overexpress ErbB2, or that demonstrate ErbB2 gene amplification (Cobleigh et al, J. Clin. Oncol., 17: 2639 (1999)). Trastuzumab binds to the extracellular domain of the ErbB2 receptor, and has been reported to exert its antitumor effects through several mechanisms. See e.g., Sliwkowski et al., Semin. Oncol. 26(Suppl 12): 60 (1999). In ErbB2 over-expressing cells, trastuzumab has been reported to down-regulate ErbB2 expression (Sarup et al., Growth Reg 1: 72 (1991); Lane et al., Mol. Cell Biol. 20: 3210 (2000)). In animal models, trastuzumab has been reported to induce antibody-dependent cell-mediated cytotoxicity against ErbB2 expressing tumor cells (Clynes et al., Nat. Med. 6: 443 (2000)). Molina et al., Cancer Research 61: 4744 (2001) report that trastuzumab reduced ECD shedding from two breast adenocarcinoma cell lines, whereas another antibody (2C4) directed against the ErbB2 ectodomain did not.

Combination therapy with trastuzumab and chemotherapy has been associated with a longer time to disease progression in breast cancer, a longer duration of response, and longer survival, compared to chemotherapy alone. Slamon et al., NEJM 344: 783 (2001). However, resistance to trastuzumab frequently occurs within the first year of treatment. See e.g., Baselga et al. Eur J Cancer, 37 Suppl 1: 18 (2001). Strategies to reduce or prevent resistance to trastuzumab are needed; one such proposed strategy is to target insulin-like growth factor I receptor (IGF-IR) signaling to delay development of trastuzumab resistance. See, e.g., Lu et al., J Natl Cancer Inst. 2001 Dec. 19; 93(24): 1852-7; Camirand et al., Med Sci Monit. 8: BR521 (2002).

Because heterodimers of ErbB2 and EGFR can elicit potent mitogenic signals, interrupting both ErbB2 and EGFR simultaneously is a potential therapeutic strategy (Earp et al., *Breast Cancer Res. Treat.*, 35: 115 (1995)). Small molecule, dual EGFR-ErbB2 tyrosine kinase inhibitors have been identified and their pre-clinical anti-tumor activities reported (Fry et al., *Proc. Natl. Acad. Sci. USA.*, 95: 12022 (1998); Cockerill et al., *Bioorganic Med. Chem. Letts.*, 11: 1401 (2001); Rusnak et al., *Cancer Res.*, 61: 7196 (2001); Rusnak et al., *Mol. Cancer Therap.*, 1: 85 (2001)).

GW572016 (lapatinib) is a potent reversible, dual inhibitor of the tyrosine kinase domains of both EGFR and ErbB2, with $IC_{50}$ values against purified EGFR and ErbB2 of 10.2 and 9.8 nM, respectively (Rusnak et al., *Mol. Cancer Therap.*, 1: 85 (2001)). Recent reports have demonstrated that GW572016 inhibits EGFR and ErbB2 autophosphorylation in tumor cell lines that overexpress these receptors (Rusnak et al., *Mol. Cancer Therap.*, 1: 85 (2001)), an effect that was primarily associated with tumor cell growth arrest. The chemical name of GW572016 is N-{3-chloro-4-[(3-fluorobenzyl)oxy]phenyl}-6-[5-({[2-methylsulfonyl)ethyl]amino}methyl)-2-furyl]-4-quinazolinamine (WO 99 35146, Carter et al.); a ditosylate form is disclosed in WO 02 02552 (McClure et al); methods of treating cancer are disclosed in WO 02/056912, and PCT/US03/10747.

SUMMARY

Figure 1:
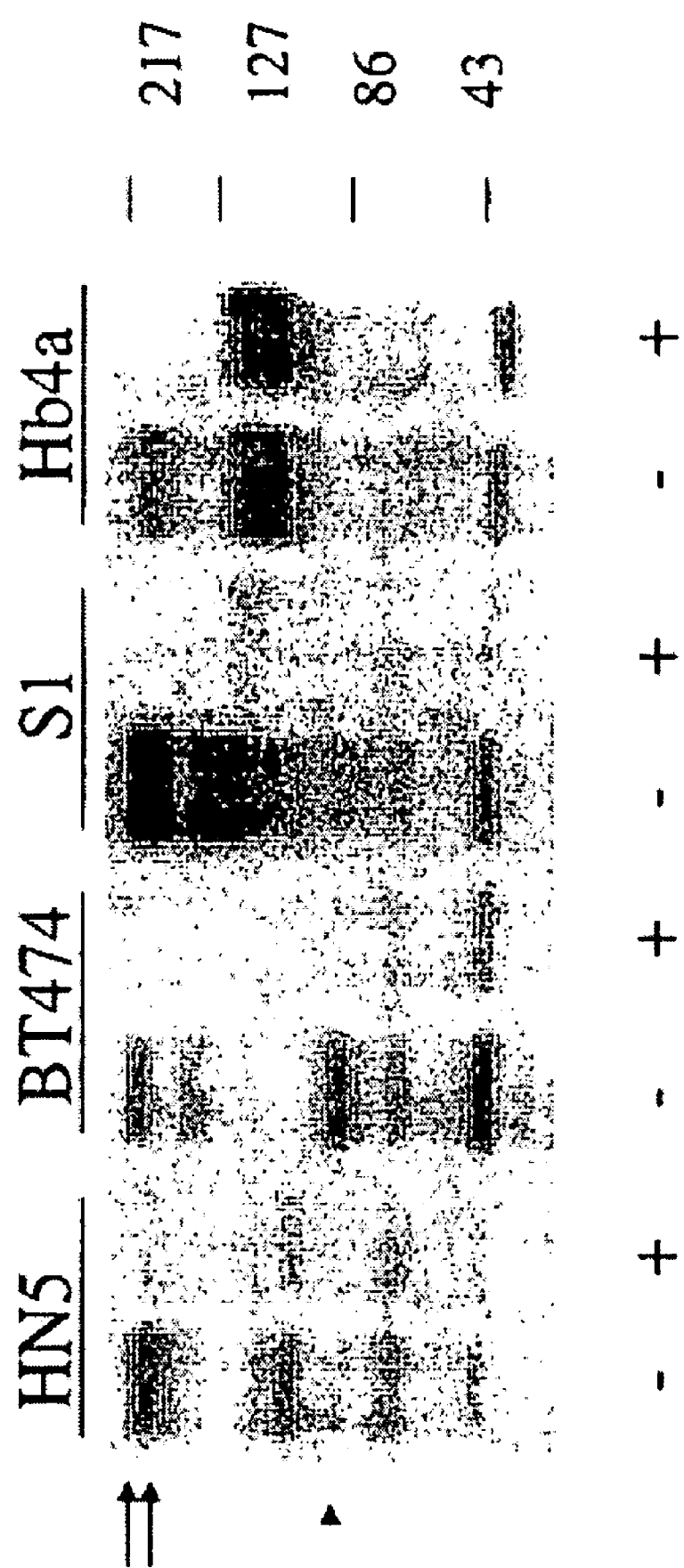
FIG. 1 shows Western Blots indicating the effects of GW572016 on the expression of phosphorylated ErbB2 (p185), phosphorylated EGFR (p170) and p95 phosphotyrosine protein in HN5 (lanes 1-2), BT474 (lanes 3-4), S1 (lanes 5-6) and Hb4a (lanes 7-8) cell lines. Western blot analysis was performed using equal amounts of protein from whole cell extracts, and using anti-pTyr monoclonal antibody. Steady state protein levels of phosphorylated $p185^{ErbB2}$ (upper arrow), $p170^{EGFR}$ (lower arrow) and p95 (arrowhead) are shown. Cells were treated with vehicle alone (DMSO at a final concentration of 0.1%) (−) or GW572106 (1 μM or 5 μM as indicated (+) in the figure) for 24 hours.

A first aspect of the present invention is a method of screening a subject needing treatment for a solid tumor, as an aid in selecting therapy. The method comprises determining whether the tumor expresses p95$^{ErbB2}$, where expression of p95$^{ErbB2}$ indicates that the subject is more likely to exhibit a favorable clinical response to treatment that includes a p95$^{ErbB2}$ inhibitor, than to treatment that does not include a p95$^{ErbB2}$ inhibitor.

A further aspect of the present invention is a method of treating a subject with a solid tumor, comprising determining whether the tumor expresses p95$^{ErbB2}$ and treating the subject with a p95$^{ErbB2}$ inhibitor if expression p95$^{ErbB2}$ is found.

A further aspect of the present invention is a method of treating a subject with a solid tumor whose tumor expresses p95$^{ErbB2}$, by administering a therapeutically effective amount of a p95$^{ErbB2}$ inhibitor to the subject.

A further aspect of the present invention is a method of treating a subject with breast cancer who has shown resistance to a p185$^{ErbB2}$ inhibitor and whose tumor expresses p95$^{ErbB2}$, by administering a therapeutically effective amount of a p95$^{ErbB2}$ inhibitor to the subject.

A further aspect of the present invention is a method of treating a subject with breast cancer that overexpresses ErbB2, where the subject has previously been treated with an ErbB2 inhibitor that interacts with the extracellular domain of ErbB2 and is now showing resistance to treatment with that ErbB2 inhibitor. The method comprises screening the subject to determine if the breast cancer expresses p95$^{ErbB2}$ and, where expression of p95$^{ErbB2}$ is found, treating the subject with a p95$^{ErbB2}$ inhibitor.

DETAILED DESCRIPTION

As shown by the examples provided herein, GW572016, a reversible, dual tyrosine kinase inhibitor of both ErbB2 and EGFR, inhibits phosphorylation of p95$^{ErbB2}$ in breast cancer cells and tumor xenografts. In contrast to GW572016, trastuzumab is shown to have limited effect on p95$^{ErbB2}$ phosphorylation. Also shown is that p95$^{ErbB2}$ differs from the full-length ErbB2 receptor in its association with other ErbB receptors. The truncated receptor (p95$^{ErbB2}$) preferentially associated with ErbB3, whereas full length p185$^{ErbB2}$ heterodimerizes with either EGFR or ErbB3. Consistent with p95$^{ErbB2}$ heterodimerization with ErbB3, it is shown that heregulin (an ErbB3 ligand) stimulates p95$^{ErbB2}$ phosphorylation in breast cancer cell lines.

Expression of the NH$_2$-terminally truncated ErbB2 receptor (p95$^{ErbB2}$) in breast cancer has been correlated with metastatic disease progression (compared to progression in disease primarily expressing full-length p185$^{ErbB2}$). GW572016 is shown to inhibit baseline p95$^{ErbB2}$ phosphorylation in breast cancer cell lines and tumor xenografts; in contrast, trastuzumab was not shown to significantly affect p95$^{ErbB2}$. Thus, p95$^{ErbB2}$ represents a target for therapeutic intervention, and is shown to be sensitive to GW572016 inhibition. Accordingly, it would be clinically beneficial to identify patients whose tumors contain elevated p95$^{ErbB2}$ levels, as an aid in providing therapy appropriately targeted to the molecular pathways active in their tumor.

The ErbB2 Receptor

Proteolytic cleavage of the ErbB2 extracellular domain, results in the expression of a truncated ErbB2 receptor (p95$^{ErbB2}$) that exerts potent oncogenic signals in preclinical models, and has been linked to metastatic disease progression in ErbB2 overexpressing breast cancers (Christianson et al., Cancer Res. 58: 5123 (1998); Molina et al., Clin. Cancer Res. 8: 347 (2002)). Whereas the role of p185$^{ErbB2}$ in regulating breast cancer cell growth and survival has been extensively studied, relatively little is known about p95$^{ErbB2}$. Here it is shown that p95$^{ErbB2}$ is constitutively activated in breast cancer cell lines and tumor xenografts. Since ErbB2 tyrosine autophosphorylation is a biochemical marker of increased transforming activity, these data implicate activated, phospho-p95$^{ErbB2}$ as playing a role in the pathophysiology of breast cancer.

Engineered truncated ErbB2 receptors possess enhanced cell transformation activity compared with p185$^{ErbB2}$ (Di Fiore et al., Science 237: 178 (1987); Bargmann and Weinberg, EMBO J. 7: 2043 (1988); Segatto et al., Mol. Cell. Biol. 8: 5570 (1988)). Deletions within the ECD of ErbB2 increase ErbB2 autokinase and transformation activities, implicating sites within the ErbB2 ECD as exerting repressive effects on ErbB2 activity. The increased oncogenic properties of p95$^{ErbB2}$ are consistent with the association of p95$^{ErbB2}$ tumor expression and metastatic disease progression in ErbB2 overexpressing breast cancers.

ErbB receptors optimally signal through heterodimeric complexes, reported to be mediated through ECD interactions. (Schaefer et al., J. Biol. Chem. 274: 859 (1999); Fitzpatrick et al., FEBS Ltt. 431: 102 (1998)). ErbB3 and p185$^{ErbB2}$ are frequently co-expressed in breast cancers (Lemoine et al., Br. J. Cancer 66: 1116 (1992); Siegel et al., EMBO J. 18: 2149 (1999); Alimandi et al., Oncogene 10: 1813 (1995); Rajkumar et al., Breast Cancer Res. Treatment 29: 3 (1995)). ErbB3-p185$^{ErbB2}$ heterodimers represent a potent mitogenic, transforming receptor complex. Since ErbB3 contains multiple binding sites for the SH2 domain of the p85 subunit of PI3K, ErbB3-containing heterodimers are potent activators of the PI3K-AKT growth and survival pathway (Soltoff et al., Mol. Cell. Biol. 14: 3550 (1994); Prigent and Gullick, EMBO J. 13: 2831 (1994)). In addition, formation of p185$^{ErbB2}$-ErbB3 heterodimers enhances the binding affinity of heregulin for ErbB3. Importantly, aberrant activation of the PI3K-AKT pathway in breast and other carcinomas predicts for a poorer clinical outcome (Vivanco and Sawyers, Nature Reviews/Cancer 2: 489 (2002); Yakes et al., Cancer Res. 62: 4132 (2002); Brognard et al., Cancer Res. 61: 3986 (2001); Cheng et al., Proc. Natl. Acad. Sci. 89: 9267 (1992)).

The Present Studies

The present studies sought to determine whether $p95^{ErbB2}$ forms heterodimers, and if so, with what heterodimeric partner. In breast cancer cell lines and BT474 tumor xenografts, it was found that $p95^{ErbB2}$ preferentially associated with ErbB3, whereas $p185^{ErbB2}$ formed heterodimers with both EGFR and ErbB3. While not wishing to be limited by a single theory, the present inventors note that these data provide an explanation as to why an ErbB3 ligand such as heregulin, but not EGF, regulates $p95^{ErbB2}$ tyrosine phosphorylation. Similarly, the fact that ErbB3 containing heterodimers potently activate the PI3K-AKT pathway provides an explanation as to why heregulin increases steady state protein levels of activated, p-AKT in breast cancer cell lines and tumor xenografts.

GW572016 is reported to inhibit the activation of EGFR, $p185^{ErbB2}$, Erk1/2, and AKT as well as reduces cyclin D protein in human tumor cell lines and xenografts (Xia et al., Oncogene 21: 6255 (2002); Rusnak et al., Cancer Res. 61: 7196 (2001); Rusnak et al., Cancer Therap. 1: 85 (2001)). Currently in clinical trials, GW572016 has shown preliminary clinical activity in pre-treated patients with metastatic cancers, most notably breast cancer (Burris, Oncologist 9 Suppl 3: 10 (2004) and unpublished data). In this context the present studies indicate that GW572016 inhibits $p95^{ErbB2}$ phosphorylation; in contrast, trastuzumab, which binds to the ECD of ErbB2, did not block $p95^{ErbB2}$ activation. While not wishing to be limited by a single hypothesis, the present inventors note that the ability of a tumor cell to signal through $p95^{ErbB2}$-containing heterodimers may contribute to trastuzumab resistance, as $p95^{ErbB2}$ would not be affected by a monoclonal antibody such as trastuzumab that is directed against the ErbB2 ECD.

The present data shed light on the role of $p95^{ErbB2}$ in the progression of breast cancer. Trastuzumab is reported to reduce ErbB2 cleavage by binding to the ErbB2 ECD (Molina et al., Cancer Res. 61: 4744 (2001)). GW572016 therapy (or combined GW572016 and trastuzumab therapy), may offer a clinical advantage over therapy with trastuzumab in the absence of a $p95^{ErbB2}$ inhibitor, by inhibiting activation of $p95^{ErbB2}$. Accordingly, in subjects who (a) exhibit trastuzumab resistance, (b) express $p95^{ErbB2}$ in tumor tissue, and/or (c) have elevated serum levels of ErbB2 ECD, treatment with GW572016 (or another $p95^{ErbB2}$ inhibitor) is indicated.

Identification of tumors expressing $p95^{ErbB2}$ may be used therefore to identify patients more likely to respond clinically to treatment that includes a $p95^{ErbB2}$ inhibitor, compared to the clinical response that would be achieved by treatment solely with an ErbB2 inhibitor that primarily inhibits full-length $p185^{ErbB2}$. ErbB2 inhibitors that act on sites retained by the truncated (p95) ErbB2 receptor would, in general, be expected to inhibit phosphorylation of $p95^{ErbB2}$, compared to ErbB2 inhibitors that act at a site on the extracellular domain of the ErbB2 receptor. A particular ErbB2 inhibitor that acts at a site retained by the truncated ErbB2 receptor is GW572016. Identification of tumors expressing $p95^{ErbB2}$ may be used to identify patients more suitable for treatment that includes a $p95^{ErbB2}$ inhibitor (such as GW572016), compared to treatment with an ErbB2 inhibitor that primarily inhibits the full-length ErbB2 receptor ($p185^{ErbB2}$). One such ErbB2 inhibitor that appears to preferentially inhibit the full-length ErbB2 receptor is the monoclonal antibody trastuzumab.

The present inventors propose that increased $p95^{ErbB2}$ mediated signaling contributes to trastuzumab resistance observed in some subjects with tumors (particularly breast cancers) that show increased serum levels of shed ErbB2 ECD, and/or that display tumor expression of $p95^{ErbB2}$. As reported herein, GW572016 inhibited $p95^{ErbB2}$ phosphorylation in both breast cancer cell lines and xenografts. Trastuzumab did not have a similar effect on $p95^{ErbB2}$, presumably because the truncated receptor protein lacks the antigen recognition site for this monoclonal antibody.

The present data show that GW572016 inhibited phosphorylation of ErbB2 (both $p185^{ErbB2}$ and $p95^{ErbB2}$), leading to downstream inhibition of p-Erk1/2, p-AKT, and cyclin D in both breast cancer cell lines and xenografts. In contrast, trastuzumab was not found to greatly affect steady state levels of phospho-ErbB2, nor did it measurably impact downstream p-Erk1/2, p-AKT, or cyclin D. GW572016 inhibited the proliferation of BT474 cells, and this effect was not completely reversed in the presence of EGF. Addition of heregulin partially reversed the inhibitory effects of GW572016 in a 72 hour assay, highlighting the importance of the ErbB2-ErbB3 signaling complex to tumor cell survival. However, prolonged incubation of BT474 cells in the presence of 1 µM GW572016 abrogated the protective effects of heregulin (data not shown), an important consideration since GW572016 is currently being administered on a daily schedule designed to achieve chronic systemic exposures of 1 µM or more in patients.

These data provide support for $p95^{ErbB2}$ playing a key role in the progression of ErbB2 overexpressing breast cancers. It is shown that a truncated $p95^{ErbB2}$ can preferentially associate with ErbB3, providing a potent signaling complex coupled to the PI3K-AKT survival pathway. In addition, the present data indicate that overexpression of heregulin or other ErbB3 ligands in the tumor microenvironment may further activate $p95^{ErbB2}$-ErbB3 heterodimers, thereby contributing to resistance to hormonal and chemotherapeutic agents through deregulation of the PI3K-AKT survival pathway. The effects of heregulin on cell signaling and the requirement of those effects on ErbB2 may be dependent upon the cell type such that the associations demonstrated in the current study may have particular relevance to breast cancer.

Trastuzumab targets the ErbB2 extracellular domain. It has been shown to reduce ErbB2 cleavage but does not appear to affect $p95^{ErbB2}$ activation-state or signaling. Identification of tumors that express $p95^{ErbB2}$ may therefore be used to select patients who should receive therapy with a $p95^{ErbB2}$ inhibitor, such as GW572016; such patients may benefit from therapy that inhibits both $p95^{ErbB2}$ and $p185^{ErbB2}$ (e.g., by using a therapeutic that inhibits both $p95^{ErbB2}$ and $p185^{ErbB2}$, or a combination of $p95^{ErbB2}$ and $p185^{ErbB2}$ inhibitors, such as combined GW572016 and trastuzumab therapy). The combination of trastuzumab and GW572016 represents a therapeutic strategy to reduce cleavage of ErbB2 via trastuzumab with concomitant inhibition of $p95^{ErbB2}$ activation and signaling by GW572016.

DEFINITIONS

As used herein, a method of screening or assessing a subject as an aid in predicting the subject's response to a therapeutic treatment, or in identifying a subject as suitable for a particular therapy, should not be confused with the use of disease prognosis markers. Certain molecular markers are known as indicators of more aggressive cancers and are associated with decreased average survival time (compared to subjects whose tumors do not express such markers). The present invention is not directed to general disease prognosis markers, but to the use of specified biological markers to assess an individual's potential for response to a therapeutic treatment, and to select treatment suitable for that individual's disease.

Methods of the present invention are directed to the identification and selection of subjects with solid tumors who are likely to respond more favorably to treatment with a $p95^{ErbB2}$ inhibitor, compared to the response that would be expected from treatment without a $p95^{ErbB2}$ inhibitor. More specifically, the methods of the present invention are directed to the identification and selection of subjects likely to respond more favorably to treatment with an ErbB2 inhibitor that is capable of inhibiting the activation of the truncated $p95^{ErbB2}$ receptor (such as GW572016), compared to the response that would be expected from treatment with an ErbB2 inhibitor that was unable to inhibit $p95^{ErbB2}$, or that primarily inhibited $p185^{ErbB2}$ and did not significantly inhibit $p95^{ErbB2}$.

More specifically, methods of the present invention are directed to assessing levels of $p95^{ErbB2}$ expression in a subject's tumor, or levels of ErbB2 ECD in the serum of a subject, where that subject is being considered for treatment of a solid tumor (particularly breast cancer) with an ErbB2 inhibitor. Subjects having elevated levels of serum ErbB2 ECD, or whose tumors express $p95^{ErbB2}$ are considered to be more likely to exhibit a favorable clinical response to treatment with a therapeutic regime that includes a $p95^{ErbB2}$ inhibitor, compared to a treatment regime that does not. More particularly, such subjects are considered to be more likely to exhibit a favorable clinical response to treatment with GW572016 (or combined GW572016 and trastuzumab treatment), compared to treatment with trastuzumab alone. In one embodiment of the present invention, the subject being assessed has previously been treated with trastuzumab or another $p185^{ErbB2}$ inhibitor, and is either has not responded clinically or has evidence of progressive disease after an initial period of clinical response (i.e., shows resistance to the therapy).

As used herein, methods to "predict" a favorable clinical response, or to "identify" suitable subjects, is not meant to imply a 100% predictive ability, but to indicate that subjects with certain characteristics are more likely to experience a favorable clinical response to a specified therapy than subjects who lack such characteristics. However, as will be apparent to one skilled in the art, some individuals identified as more likely to experience a favorable clinical response will nonetheless fail to demonstrate measurable clinical response to the treatment.

As used herein, a subject refers to a mammal, including humans, canines and felines. Preferably subjects treated with the present methods are humans.

As used herein, a 'favorable response' (or 'favorable clinical response') to an anticancer treatment refers to a biological or physical response that is recognized by those skilled in the art as indicating a decreased rate of tumor growth, compared to tumor growth that would occur with an alternate treatment or the absence of any treatment. "Favorable clinical response" as used herein is not meant to indicate a cure. A favorable clinical response to therapy may include a lessening of symptoms experienced by the subject, an increase in the expected or achieved survival time, a decreased rate of tumor growth, cessation of tumor growth (stable disease), regression in the number or mass of metastatic lesions, and/or regression of the overall tumor mass (each as compared to that which would occur in the absence of therapy).

As is well known in the art, tumors are frequently metastatic, in that a first (primary) locus of tumor growth spreads to one or more anatomically separate sites. As used herein, reference to "a tumor" in a subject includes not only the primary tumor, but metastatic tumor growth as well.

As used herein, an ErbB2 inhibitor is an agent that inhibits or reduces the formation of p-Tyr/ErbB2 (activated ErbB2), compared to the formation of p-Tyr/ErbB2 that would occur in the absence of the ErbB2 inhibitor. Such inhibitors include small chemical molecules and biologic agents such as monoclonal antibodies. As used herein, a $p95^{ErbB2}$ inhibitor is an agent that inhibits or reduces the formation of p-Tyr/$p95^{ErbB2}$ (activated $p95^{ErbB2}$), compared to the formation of p-Tyr/$p95^{ErbB2}$ that would be formed in the absence of the agent. As used herein, a $p185^{ErbB2}$ inhibitor is an agent that inhibits or reduces the formation of p-Tyr/$p185^{ErbB2}$ (activated $p185^{ErbB2}$), compared to the formation of p-Tyr/$p185^{ErbB2}$ that would be formed in the absence of the agent. An agent may be both a $p95^{ErbB2}$ inhibitor and a $p185^{ErbB2}$ inhibitor.

As used herein, a cell "overexpressing" ErbB2 refers to a cell having a significantly increased number of functional ErbB2 receptors, compared to the average number of receptors that would be found on a cell of that same type. Overexpression of ErbB2 has been documented in various cancer types, including breast (Verbeek et al., *FEBS Letters* 425: 145 (1998); colon (Gross et al., *Cancer Research* 51: 1451 (1991)); lung (Damstrup et al., *Cancer Research* 52: 3089 (1992), renal cell (Stumm et al, Int. *J. Cancer* 69: 17 (1996), Sargent et al., *J. Urology* 142: 1364 (1989)) and bladder (Chow et al., *Clin. Cancer Res.* 7: 1957 (2001); Bue et al., *Int. J. Cancer,* 76: 189 (1998); Turkeri et al., *Urology* 51: 645 (1998)). Overexpression of ErbB2 may be assessed by any suitable method as is known in the art, including but not limited to imaging, gene amplification, number of cell surface receptors present, protein expression, and mRNA expression. See e.g., Piffanelli et al., *Breast Cancer Res. Treatment* 37: 267 (1996).

The DAKO HercepTest® (DakoCytomation, Denmark), is an FDA approved IHC assay for the evaluation of ErbB2 protein overexpression, and provides semi-quantitative results of $p185^{ErbB2}$ overexpression by light microscopy. Samples are scored as from 0 (no staining, negative), 1+ (weak staining, negative), 2++ (weakly positive) and 3+++ (strongly positive). Typically patients with 2++ or 3+++ results are considered to be overexpressing ErbB2 and thus suitable for treatment with trastuzumab. Accordingly, a cell that 'overexpresses' $p185^{ErbB2}$ is one that would score 2++ or 3+++ on the HercepTest®, or achieve a comparable score using another assay.

As used herein, "solid tumor" does not include leukemia or other hematologic cancers.

As used herein, an "epithelial tumor" is one arising from epithelial tissue.

Inhibitors of ErbB2 used in the present methods should preferentially inhibit phosphorylation of tyrosine residues within the kinase domain, which are the residues implicated in regulating downstream MAPK/Erk and PI3K/AKT pathways.

Non-ErbB transactivating factors (such as growth hormone, which is increased in many cancer patients) regulate phosphorylation of tyrosine residues external to the catalytic kinase domain (e.g., Y992, Y1068, Y1148, and Y1173). When conducting immunohistochemistry (IHC) to assess the phosphorylation state of ErbB2, the use of anti-receptor antibodies that are not domain specific will not distinguish between phosphorylation events in tyrosine residues in the kinase domain and those external to the kinase domain; in this situation the overall phosphorylation state of EGFR and ErbB2 may appear unchanged even when key residues within the kinase domain that regulate downstream Erk and AKT pathways have been inhibited. Accordingly, the use of antibodies that are domain specific is preferred when IHC is utilized in the methods of the present invention.

Methods of Measuring ECD and p95

The identification of subjects whose tumors express p95 (truncated ErbB2) may be achieved using any suitable means as is known in the art. One such method is to assess the levels of circulating ErbB2 ECD in serum of subjects, where an elevated level of ECD indicates that the subject's tumor contains truncated ErbB2, and thus treatment that includes a $p95^{ErbB2}$ inhibitor such as GW572016 is preferred to a treatment regime that does not include a $p95^{ErbB2}$ inhibitor. Alternatively, the presence of truncated ErbB2 in the tumor tissue may be detected directly, e.g., by using Western blot techniques as described herein.

ErbB2 ECD may be detected in the serum of subjects using any suitable technique known in the art. Serum ECD may be measured, for example, using an enzyme immunoassay. Various groups have developed assays that detect the ECD of ErbB2, using monoclonal antibodies that react with the external domain of ErbB2. See, e.g., Hayes, et al., Clin. Cancer Res. 7: 2703 (2001); Hayes et al., Breast Cancer Res. Treat., 14: 135a 1989; Carney et al., J. Tumor Marker Oncol., 6: 53 (1991); Leitzel et al., J. Clin. Oncol., 10: 1436, (1992); Yamauchi et al., J. Clin. Oncol., 15: 2518 (1997).

Harris et al. (J. Clin. Oncol. 19: 1698 (2001)), in a study of 425 patients with measurable, metastatic breast cancer, assayed serum samples for ErbB2 ECD using an enzyme-linked immunoassay kit (Bayer Diagnostics, Walpole, Mass.). Colomer et al. (Clin. Cancer Research, 6: 2356 (2000) used a sandwich enzyme immunoassay (Human neu quantitative ELISA, Calbiochem; Carney et al., J. Tumor Mark. Oncol. 6: 53 (1991)), and found circulating ECD levels of from 155 to 38,871 fmol/ml (median 427 fmol/ml) in samples from 58 patients with metastatic breast cancer. Using 450 fmol/ml as the cut-off for "elevated" circulating ECD levels, Colomer et al. found that 41% of their subjects had elevated ECD levels.

Hayes et al., (Clin. Canc. Res. 7: 2703 (2001)) assayed plasma samples from 242 metastatic breast cancer patients for circulating ErbB2 ECD levels, using a sandwich enzyme immunoassay. The assay utilized MAb NB3 bound to 96-well plate and enzyme-linked MAb TA1 as a tracer. On the basis of previous studies, Hayes et al. utilized a cutoff of 10.5 ng/ml (mean+2 SD in healthy subjects) to distinguish elevated from nonelevated levels (Carney et al., J. Tumor Marker Oncol., 6: 53 (1991)). Eighty-nine (37%) of the 242 patients had elevated ErbB2 ECD levels.

Accordingly, an "elevated" level of serum ErbB2 ECD for a subject with a given disease may be defined as a level greater than the median level seen in subjects with the same gross disease; as a level which is greater than or equal to the mean plus two standard deviations found in healthy subjects; or alternatively as a level that has been associated with improved response to treatment that includes a $p95^{ErbB2}$ inhibitor (compared to the response that would be obtained in the absence of a $p95^{ErbB2}$ inhibitor). For any particular disease, the level of serum ErbB2 ECD that is correlated with such an improved response to $p95^{ErbB2}$ inhibitor treatment can be determined by one skilled in the art, using methods known in the art.

Alternatively or in addition to assessing the levels of ErbB2 ECD in serum of subjects, the presence of truncated ErbB2 in the tumor tissue may be assessed. The relative level of truncated ErbB2 may be assessed by comparing whether truncated receptor is expressed at a certain level relative to the expression of the entire (p185) ErbB2 receptor. See, e.g., Christianson et al., Cancer Res. 15: 5123 (1998); Molina et al., Cancer Res. 61: 4744 (2001). Accordingly, cells that express (or 'overexpress') $p95^{ErbB2}$ can be defined as those in which the truncated ErbB2 receptor is expressed at a level at least equal to about 5%, 10%, 20%, 25% or more of full-length ErbB2 receptor expression.

One method of detecting $p95^{ErbB2}$ levels in tissue samples utilizes immunohistochemistry, a staining method based on immunoenzymatic reactions using monoclonal or polyclonal antibodies to detect cells or specific proteins such as tissue antigens. Typically, immunohistochemistry protocols include detection systems that make the presence of the markers visible (to either the human eye or an automated scanning system), for qualitative or quantitative analyses. Various immunoenzymatic staining methods are known in the art for detecting a protein of interest. For example, immunoenzymatic interactions can be visualized using different enzymes such as peroxidase, alkaline phosphatase, or different chromogens such as DAB, AEC or Fast Red.

The methods of the present invention may be accomplished using any suitable method or system of immunohistochemistry, as will be apparent to one skilled in the art, including automated systems, quantitative IHC, semi-quantitative IHC, and manual methods.

As used herein, "quantitative" immunohistochemistry refers to an automated method of scanning and scoring samples that have undergone immunohistochemistry, to identify and quantitate the presence of a specified biomarker, such as an antigen or other protein. The score given to the sample is a numerical representation of the intensity of the immunohistochemical staining of the sample, and represents the amount of target biomarker present in the sample. As used herein, Optical Density (OD) is a numerical score that represents intensity of staining. As used herein, semi-quantitative immunohistochemistry refers to scoring of immunohistochemical results by human eye, where a trained operator ranks results numerically (e.g., as 1, 2 or 3).

Various automated sample processing, scanning and analysis systems suitable for use with immunohistochemistry are available in the art. Such systems may include automated staining and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples. See, e.g., the CAS-200 system (Becton, Dickinson & Co.).

Where phosphorylated proteins are being assayed, tissue must be processed in a manner that allows accurate detection of phosphorylated proteins. E.g., if the tissue sample is paraffin-embedded, it may be fixed in the presence of phosphatase inhibitors and in a neutralized buffered formalin solution.

Treatment of Subjects

The present invention provides a method of screening subjects who are being considered for treatment with an ErbB2 inhibitor for a solid tumor, to identify those subjects who are likely to respond more favorably to therapy that includes a $p95^{ErbB2}$ inhibitor (such as GW572016), compared to therapy that does not include such an inhibitor. Stated another way, the present invention provides a method of screening an individual subject in need of such treatment for a solid tumor, to identify whether the subject is likely to respond favorably to treatment with a p95$^{ErbB2}$ inhibitor, as an aid in clinical decision-making.

The methods of the present invention are suitable for use in subjects afflicted with a solid tumor, particularly one of epithelial origin, that expresses ErbB2. In one embodiment of the present invention, the subject is afflicted with a solid tumor of epithelial origin that overexpresses ErbB2. In one preferred embodiment, the subject is afflicted with breast cancer, where the breast cancer cells overexpress p185$^{ErbB2}$ and express p95$^{ErbB2}$ The methods of the present invention comprise determining prior to treatment whether a subject's tumor expresses p95$^{ErbB2}$, e.g., by measuring either circulating ErbB2 ECD or measuring p95$^{ErbB2}$ expression in tumor tissue. Any suitable method of determining the level of truncated ErbB2 (and/or circulating ErbB2 ECD) may be utilized in the present methods.

According to one embodiment of the present methods, the pre-treatment level of p95$^{ErbB2}$ (or ErbB2 ECD) is assessed immediately before the subject begins a course of anti-neoplastic therapeutic treatment. As used herein, 'immediately' before treatment refers to a biologically relevant time frame. Preferably the assessment is done within about three months, two months, or six weeks prior to treatment, more preferably within about four weeks, three weeks, two weeks, ten days or less prior to treatment. Alternatively in the methods of the present invention, the level of the specified marker may be assessed after treatment has begun, to ascertain whether the appropriate treatment is being used.

As is known in the art, clinical use of an antineoplastic agent typically involves repeated administration of the agent to a subject over a set time period, on a pre-established schedule. Therapeutic agents may be administered in any suitable method, including but not limited to intravenously (intermittently or continuously) or orally. For example, a 'course' of a certain therapeutic agent may require daily administration of the agent for two weeks; a course of therapy using a different therapeutic agent or for a different tumor type may involve once weekly administration for six weeks. As used herein, a "course" of therapy refers to a therapeutic schedule (dosage, timing of administration, and duration of therapy) that is specific to the therapeutic agent being used and/or the tumor type being treated, and that is accepted in the art as therapeutically effective. Such schedules are developed using pharmacologic and clinical data, as is known in the art. A subject may undergo multiple courses of treatment over time, using the same or different therapeutic agents, depending on whether disease progression occurs.

The present methods are suitable for use in subjects undergoing their first course of antineoplastic treatment, or subjects who have previously received a course of antineoplastic treatment for a tumor.

The present methods are suited for use with any form of ErbB2 inhibitors, including organic molecules such as GW572016, monoclonal antibodies, or other chemical or biological therapeutic agents. Specific inhibitors, as well as processes of making thereof, are provided in U.S. Pat. No. 6,169,091; U.S. Pat. No. 6,174,889; U.S. Pat. No. 6,207,669; U.S. Pat. No. 6,391,874; WO 99/35146; WO 01/04111.

Example 1

Materials and Methods

Materials

HN5, an EGFR overexpressing LICR-LON-HN5 head and neck carcinoma cell line was kindly provided by Helmout Modjtahedi at the Institute of Cancer Research, Surrey, U.K. The ErbB2 overexpressing human breast adenocarcinoma cell line, BT474 was obtained from the American Type Culture Collection (Manassas, Va., USA). HB4a cells are derived from human mammary luminal tissue; ErbB2 transfection of parental HB4a cells yielded the HB4a C5.2 cell line (Harris et al., Int J Cancer. 80: 477 1999). S1 cells, which express elevated levels of p-ErbB2 were established by sub-cloning HB4a C5.2 (Xia et al., Oncogene, 21: 6255 (2002)). EGF was purchased from Sigma Chemical (St. Louis, Mo., USA). Recombinant human NRG-1-B1/HRGB1 EGFR domain (heregulin, HRG) was from RD system (Minneapolis, Minn., USA). Anti-phosphotyrosine antibody was purchased from Sigma and Upstate (Lake Placid, N.Y., USA). Anti-EGFR (Ab-12) and anti-c-ErbB2 (Ab-11) monoclonal antibodies were from Neo Markers (Union City, Calif., USA). Anti-ErbB2 (AA1243-1255), anti-phospho-ErbB2 (Y1248), and anti-cyclin D1/2 were from Upstate. Anti-phospho-AKT (Ser 437) monoclonal antibody was from Cell Signaling Technology, Inc. (Beverly, Mass., USA). Anti-AKT1/2, anti-phospho-Erk1/2, anti-Erk1 and anti-Erk2 antibodies were purchased from Santa Cruz Biotechnology, Inc. (Santa Cruz, Calif., USA). Trastuzumab was purchased from Genentech, Inc. (South San Francisco, Calif., USA). SuperSignal West Femto Maximum Sensitivity Substrate was from Pierce (Rockford, Ill., USA). Protein G agarose was purchased from Boehringer Mannheim (Germany). IRDye800 Conjugated Affinity Purified Anti-Rabbit IgG and anti Mouse IgG were from Rockland (Gilbertsville, Pa., USA). Alexa Fluor680 goat anti-rabbit IgG was obtained from Molecular Probes (Eugene, Oreg., USA). GW572016, N-{3-Chloro-4-[(3-fluorobenzyl)oxy]phenyl}-6-[5-({[2-(methylsulfonyl)ethyl] amino}methyl)-2-furyl]-4-quinazolinamine, was synthesized as previously described. GW572016 for cell culture work was dissolved in DMSO.

Cell Cultures

BT474 cells were cultured in RPMI 1640 supplemented with L-glutamine, 10% FBS (Hyclone) and 5 μ/ml insulin. HB4a cells were cultured under identical conditions to BT474 cells, in addition, with 10 μg/ml hydrocortisone. S1 cells were cultured in RPMI 1640 supplemented with L-glutamine, 10% FBS and 50 μg/ml hygromycin. HN5 cells were cultured in DMEM supplemented with high glucose and 10% fetal bovine serum (FBS). All cell cultures were maintained in a humidified atmosphere of 5% $CO_2$ at 37° C.

EGF and HRG Stimulation Experiments

Cells were seeded at low density in serum free-medium supplemented with 1.5% BSA, and then exposed for 6-24 h to GW572016 at various concentrations indicated in the figure legends, or 10 μg/ml trastuzumab. Cells were stimulated with 50 ng/ml EGF or 5 nM HRG for 15 minutes, harvested on ice, and then lysed in RIPA buffer (150 mM NaCl, 50 mM Tris-HCl, pH 7.5, 0.25% (w/v) deoxycholate, 1% NP-40, 5 mM sodium orthovanadate, 2 mM sodium fluoride, and a protease inhibitor cocktail).

Immunoprecipitation and Western Blots

Immunoprecipitations and Western blots were performed as previously described (Xia et al., *Oncogene*, 21: 6255 (2002)). Briefly, protein concentrations were determined using a modification of the Bradford method (Bio-Rad Laboratory) and equal amounts of protein subjected to immunoprecipitation and Western blot. Efficiency and equal loading of proteins was evaluated by Ponceau S staining. Membranes were blocked for 1 h in TBS (25 mM Tris-HCl, pH 7.4, 150 mM NaCl, 2.7 mM KCl) containing 4% (w/v) lowfat milk or 3% BSA (w/v). Membranes were then probed with specific antibodies recognizing target proteins, which were visualized with the SuperSignal West Femto Maximum sensitivity substrate kit (Pierce). Other blots were visualized using the Odyssey Infrared Imaging System (LI-COR, Inc., Lincoln, Nebr., USA). For the Odyssey, membranes were incubated with fluorescent-labeled secondary antibody at 1:10000 dilution with 3% BSA in PBS for 60 min protected from light. After washing in PBS+0.1% tween-20, the membranes were scanned using an Odyssey imaging system.

Tumor Xenografts

BT474 tumors were maintained by serial passage of fragments into female C.B-17 SCID mice, for up to 10 passages. Once tumor implants were palpable, mice were administered either vehicle (0.5% hydroxypropylmethylcellulose/0.1% Tween 80) given orally (PO), five doses of GW572016 at 100 mg/kg (PO) twice daily at 8 hour intervals, or trastuzumab at 100 mg/kg given intraperitoneally (IP) daily for 3 days. Tumors were removed 4 hours after the last dose, frozen in liquid Nitrogen, and stored at −80° C. until analysis. For the terminal biopsy, mice were euthanized with $CO_2$ inhalation. Cell extracts were prepared by homogenization in RIPA buffer at 4° C.

Example 2

Inhibition of p95 by GW572016

FIG. 1 demonstrates the effects of GW572016 on the expression of phospho-ErbB2 (p185), EGFR (p170), and p95 in BT474, HN5, S1 and Hb4a cell lines. Western blot analysis was performed using equal amounts of protein from whole cell extracts using anti-pTyr monoclonal antibody. Steady state protein levels of phosphorylated $p185^{ErbB2}$ (top arrow), $p170^{EGFR}$ (lower arrow) and p95 (arrowhead) are shown in FIG. 1. Cells were treated with vehicle alone (DMSO at a final concentration of 0.1%; indicated by "−") or GW572016 (1 µM for BT474; 5 µM for other cell lines, indicated by "+") for 24 hours.

As shown in FIG. 1 (compare lanes 3 and 4), treating ErbB2 overexpressing BT474 breast cancer cells with 1 µM GW572016 inhibited not only $p185^{ErbB2}$ phosphorylation (top arrow) but also inhibited a 95 kDa phosphotyrosine protein (p95, arrowhead).

In S1 cells, treatment with 5 µM GW572016 inhibited $p185^{ErbB2}$ and p95 phosphorylation (FIG. 1, compare lanes 5 and 6). S1 cells are a cell line established by single cell cloning of Hb4ac5.2 cells, a non-malignant mammary epithelial line stably transfected with ErbB2 (Xia et al., 2002).

In contrast, p95 was not identified in the EGFR-overexpressing head and neck squamous cell carcinoma line HN5 (FIG. 1, lanes 1 and 2) or in parental Hb4a cells (lanes 7 and 8). However, 5 µM GW572016 inhibited phosphorylation of $p170^{EGFR}$ and $p185^{ErbB2}$, respectively, in these cells (FIG. 1).

Example 3

Identification of p95 as the Truncated ErbB2 Receptor $p95^{ErbB2}$

Proteolytic cleavage of the extracellular domain of $p185^{ErbB2}$ leads to the appearance of the truncated 95 kDa ErbB2 receptor ($p95^{ErbB2}$), which is highly phosphorylated (Christianson et al., Cancer Res. 58: 5123 (1998)). To determine whether the 95 kDa phosphotyrosine protein as identified in the Example 1 was $p95^{ErbB2}$, equal amounts of protein from total cell extracts were subjected to Western blot analysis using anti-ErbB2 mAbs that recognized distinct epitopes.

Figure 2:
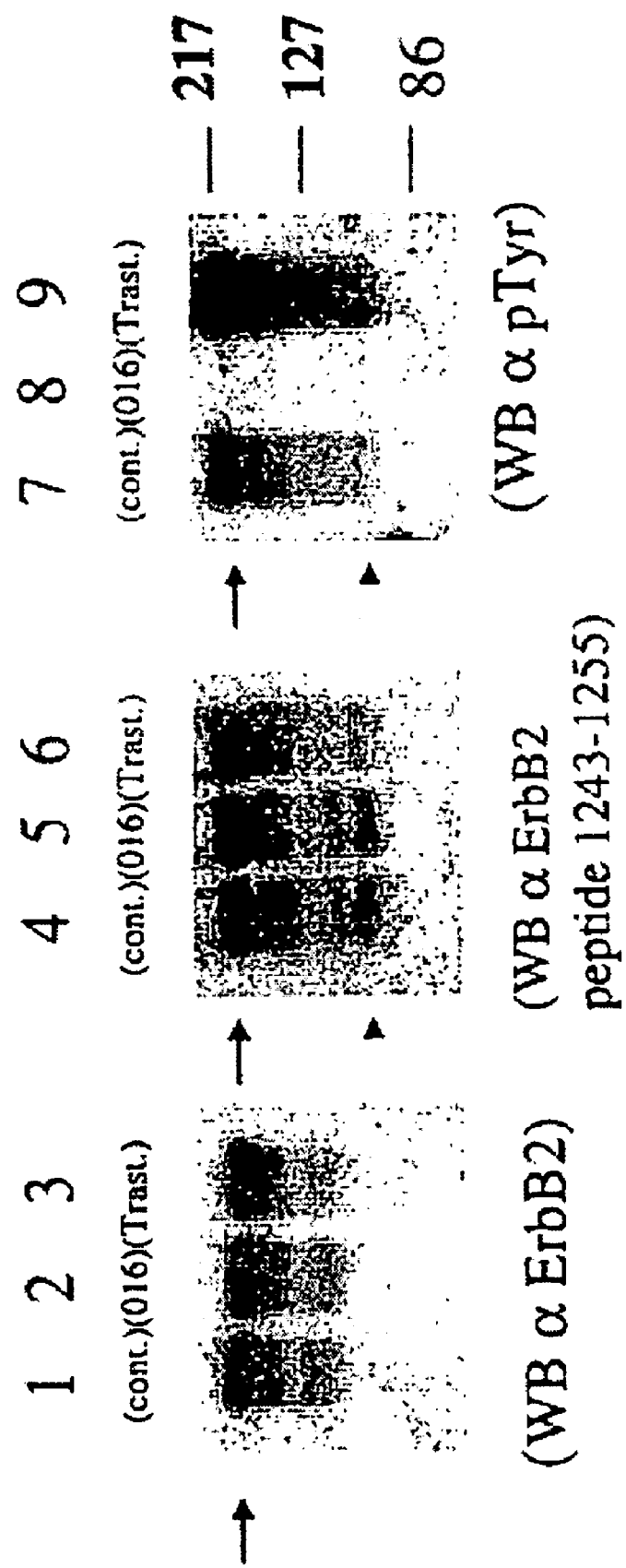
FIG. 2 shows Western Blots indicating the effects of GW572016 or trastuzumab on ErbB2, $p95^{ErbB2}$, pTyr/$p95^{ErbB2}$, and pTyr/ErbB2 in BT474 cells. Exponentially growing BT474 cells were co-cultured for 24 hours with either 0.5 μM GW572016 (lanes 2, 5, 8; "016"), 10 ug/ml trastuzumab (lanes 3, 6, 9; "Trast."), or control vehicle (0.1% DMSO; lanes 1, 4, 7, "cont."). Equal amounts of protein were separated by SDS-PAGE and then ErbB2, $p95^{ErbB2}$, pTyr/$p95^{ErbB2}$, and pTyr/ErbB2 steady state protein levels were assessed by Western blot. Blots were probed with the following antibodies: anti-ErbB2 ECD (lanes 1-3), anti-intracytoplasmic ErbB2 peptide (aa 1243-1255) (lanes 4-6), and anti-pTyr (lanes 7-9). Along the left sides of the lanes, the uppermost arrow indicates $p185^{ErbB2}$; lower arrowhead indicates $p95^{ErbB2}$. Molecular weights are indicated on the right side of the figure.

As shown in FIG. 2, exponentially growing BT474 cells were co-cultured for 24 hours with vehicle alone (0.1% DMSO; lanes 1, 4 and 7), 0.5 µM GW572016 (lanes 2, 5 and 8), or 10 µg/ml trastuzumab (lanes 3, 6 and 9). Equal amounts of protein were separated by SDS-PAGE and then ErbB2, $p95^{ErbB2}$, $pTyr/p95^{ErbB2}$, and pTyr/ErbB2 steady state protein levels were assessed by Western blot. Blots were probed with the following monoclonal antibodies: (a) anti-ErbB2 ECD (lanes 1-3), (b) anti-intracytoplasmic ErbB2 peptide (amino acids 1243-1255, an intra-cytoplasmic ErbB2 sequence distinct from EGFR or ErbB3) (lanes 4-6), or (c) anti-pTyr (lanes 7-9). Along the left side of the lanes, the uppermost arrow indicates p185; lower arrowhead indicates p95. Molecular weights are indicated on the right side of the figure.

As shown in FIG. 2 (lanes 1-3), using the anti-ErbB2 ECD mab indicated that steady-state $p185^{ErbB2}$ protein levels (arrow) did not vary among BT474 control cells (lane 1), cells treated with 0.5 µM GW572016 (lane 2), and cells treated with 10 µg/ml trastuzumab (lane 3). However, p95 was not identified using this particular mAb.

As shown in FIG. 2 (lanes 4-6), using the anti-ErbB2 mab recognizing peptide 1243-1255, both $p185^{ErbB2}$ (arrow) and p95 (arrowhead) were identified in Western blots from BT474 whole cell extracts. These results indicate that p95 is the truncated ErbB2 receptor, $p95^{ErbB2}$. BT474 cells treated with trastuzumab (10 µg/ml; lane 6) exhibited reduced $p95^{ErbB2}$ steady state protein levels (lane 6).

As shown in FIG. 2 (lanes 7-9), using the anti-pTyr mab indicates that whereas tyrosine phosphorylation of both $p185^{ErbB2}$ and $p95^{ErbB2}$ was inhibited by GW572016 (0.5 µM) (compare lanes 7 and lane 8), trastuzumab did not have a similar inhibitory effect (compare lanes 7 and 9).

The above data indicate that the 95 kDa phosphotyrosine protein shown to be GW572016-sensitive is the truncated ErbB2 receptor, $p95^{ErbB2}$ Example 4

Figure 3A:
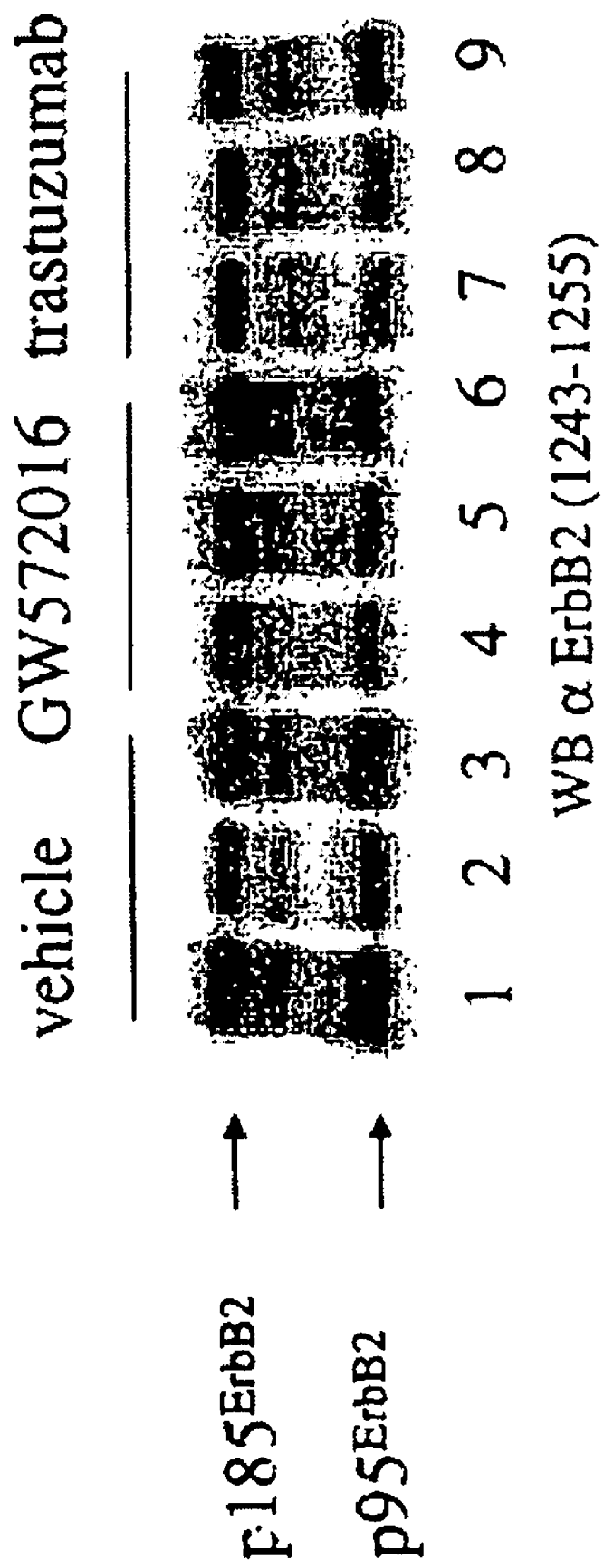
FIG. 3a shows Western Blots indicating the effects of GW572016 or trastuzumab on $p95^{ErbB2}$ and $p185^{ErbB2}$ protein levels in BT474 tumor xenografts established in CD-1 nude mice. When tumors were palpable, animals were administered either vehicle alone (lanes 1-3), GW572016 (lanes 4-6), or trastuzumab (lanes 7-9). Total $p185^{ErbB2}$ and $p95^{ErbB2}$ steady state protein levels were assessed by Western blot using an antibody recognizing an intracytoplasmic peptide (aa 1243-1255) of ErbB2.
Figure 3B:
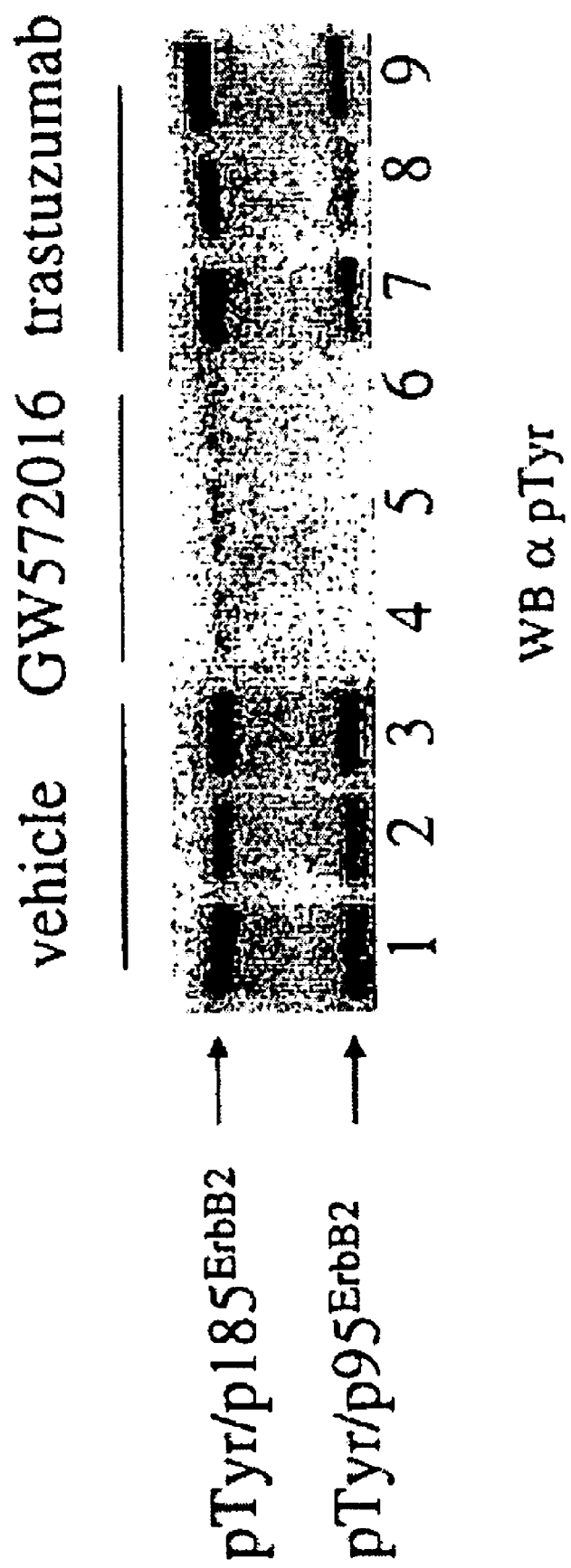
FIG. 3b shows Western Blots indicating the effects of GW572016 or trastuzumab on phosphorylated $p95^{ErbB2}$ and phosphorylated $p185^{ErbB2}$ protein levels in BT474 tumor xenografts established in CD-1 nude mice. When tumors were palpable, animals were administered either vehicle alone (lanes 1-3), GW572016 (lanes 4-6), or trastuzumab (lanes 7-9) Activated $p185^{ErbB2}$ (pTyr/$p185^{ErbB2}$) and $p95^{ErbB2}$ (pTyr/$p95^{ErbB2}$) were assessed using an anti-pTyr mAb.
Figure 3C:
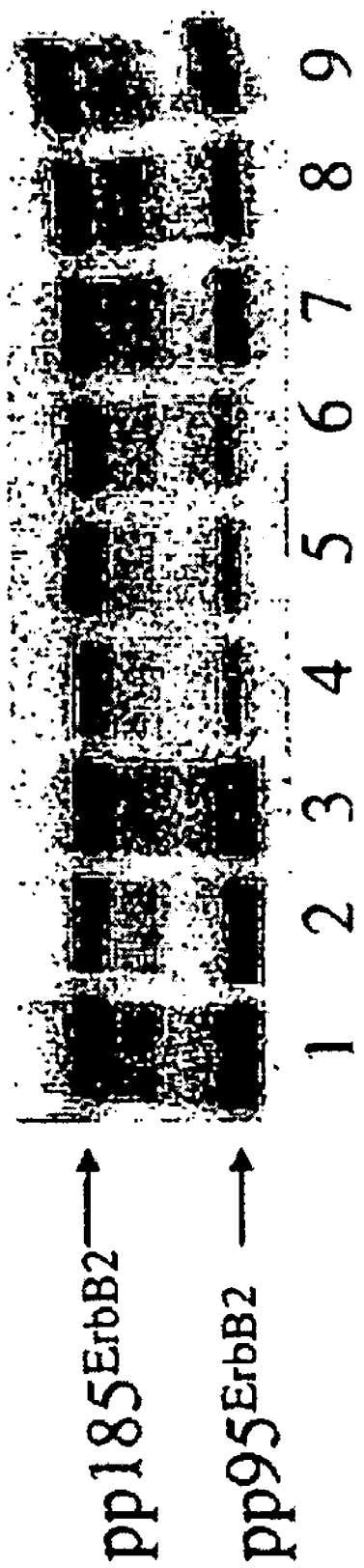
FIG. 3c shows Western Blots indicating the effects of GW572016 or trastuzumab on phosphorylated $p95^{ErbB2}$ and phosphorylated $p185^{ErbB2}$ protein levels in BT474 tumor xenografts established in CD-1 nude mice. When tumors were palpable, animals were administered either vehicle alone (lanes 1-3), GW572016 (lanes 4-6), or trastuzumab (lanes 7-9). Phosphorylated $p95^{ErbB2}$ and $p185^{ErbB2}$ were assessed using an anti-phospho-tyrosine specific monoclonal antibody recognizing Y1248.

GW572016 Inhibits Both $p95^{ErbB2}$ and $p185^{ErbB2}$ in Breast Cancer Xenografts As shown in FIGS. 3a-3c, the in vivo effects of GW572016 on $p95^{ErbB2}$ were examined in mice bearing established BT474 tumor implants. BT474 tumor xenografts were established in CD-1 nude mice. When tumors were palpable, animals were administered vehicle alone (lanes 1-3), GW572016 ((100 mg/kg/dose; lanes 4-6), or trastuzumab (lanes 7-9). Total $p185^{ErbB2}$ and $p95^{ErbB2}$ steady state protein levels were assessed by Western blot using three different monoclonal antibodies: in FIG. 3a, the mab recognized an intracytoplasmic peptide (aa 1243-1255) of ErbB2; in FIG. 3b, anti-phosphotyrosine mab was used to assess activated $p185^{ErbB2}$ ($pTyr/p185^{ErbB2}$) and $p95^{ErbB2}$ ($pTyr/p95^{ErbB2}$); in FIG. 3C, phosphorylated $p95^{ErbB2}$ and $p185^{ErbB2}$ were assessed using an anti-phosphotyrosine specific mAb recognizing Y1248.

As shown in FIG. 3a, steady state protein levels of total $p185^{ErbB2}$ and $p95^{ErbB2}$ were unchanged in tumor xenografts from vehicle (lanes 1-3), GW572016 (lanes 4-6), or trastuzumab (lanes 7-9) treated mice.

As shown in FIG. 3b, phospho-$p185^{ErbB2}$ steady state protein levels were inhibited in BT474 tumor xenografts from GW572016 treated mice (compare lanes 4-6 to other lanes). Similarly, GW572016 inhibited phospho-$p95^{ErbB2}$ steady state protein levels (compare lanes 4-6 to other lanes). Trastuzumab did not appear to inhibit phospho-p185$^{ErbB2}$ expression (compare lanes 7-9 to control lanes 1-3).

As shown in FIG. 3c, the effect of GW572016 on tyrosine 1248 (Y1248), a key ErbB2 autophosphorylation site linked to downstream MAPK-Erk1/2 signaling, was also investigated. GW572016 (100 mg/kg/dose) inhibited Y1248 phosphorylation in p95$^{ErbB2}$ (compare lanes 4-6 to other lanes), whereas trastuzumab did not appear to have any marked effect (compare lanes 7-9 to control lanes 1-3).

In BT474 tumor cell xenografts, inhibition of p185$^{ErbB2}$ and p95$^{ErbB2}$ phosphorylation by GW572016 also blocked activation of downstream signaling pathways involved in tumor cell growth and survival (MAPK-Erk1/2 and PI3K-AKT), and reduced cyclin D1/2 total steady state protein levels. Equal amounts of protein from tumor xenograft whole cell extracts were separated by SDS-PAGE and steady state protein levels of total and phosphorylated forms Erk1/2 and AKT were assessed by Western blot. Cyclin D1/2 steady state protein levels were also determined. Steady state protein levels of actin confirmed equal loading of protein.

Figure 4:
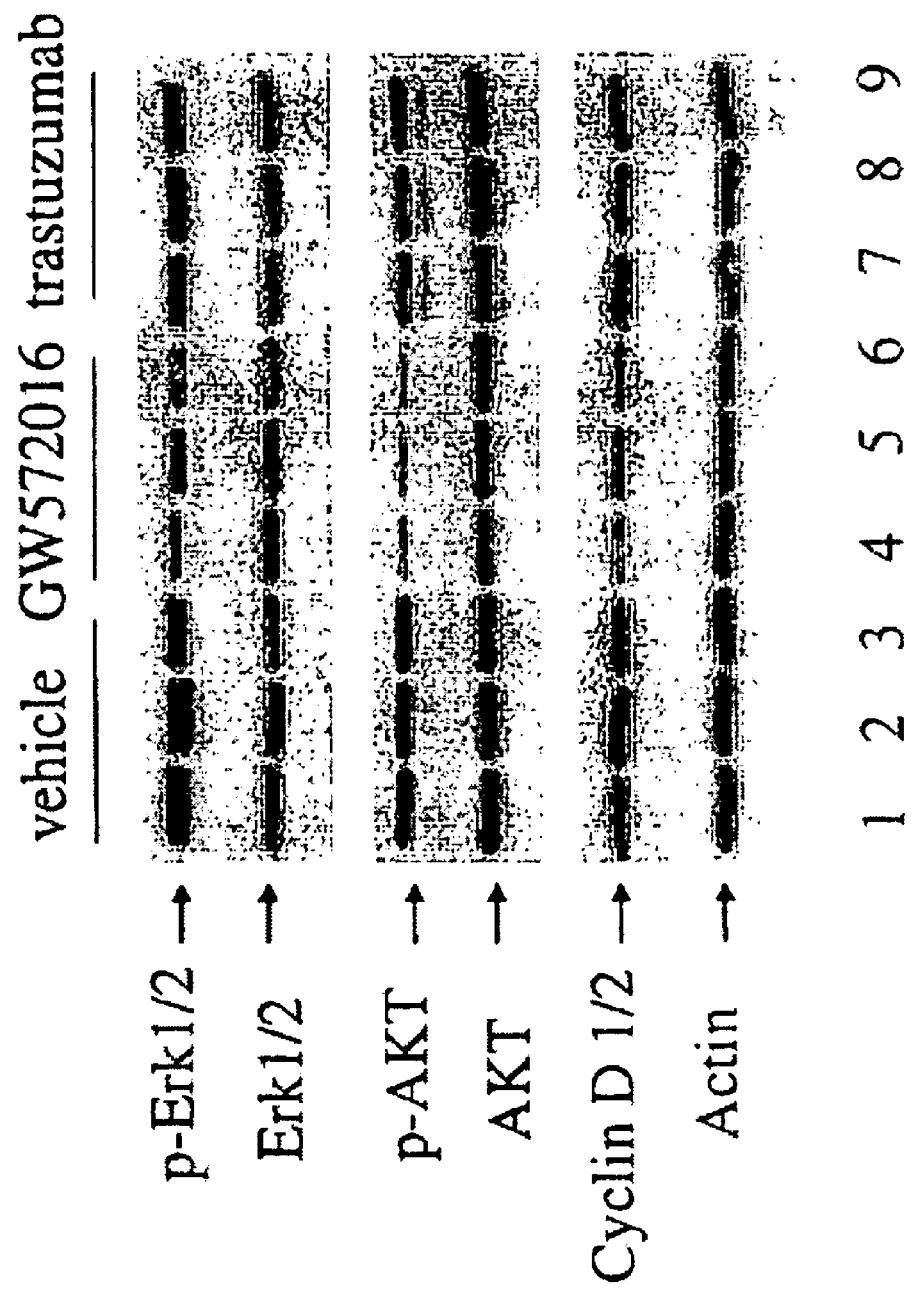
FIG. 4 shows Western Blots indicating the effects of GW572016 on activation of MAPK-Erk1/2 and PI3K-AKT pathways, and on cyclin D1/2 total steady state protein levels in BT474 xenografts. Animals were administered either vehicle alone (lanes 1-3), GW572016 (lanes 4-6), or trastuzumab (lanes 7-9). Equal amounts of protein from tumor xenograft whole cell extracts were separated by SDS-PAGE and steady state protein levels of total and phosphorylated forms of Erk1/2 and AKT were assessed by Western blot. Cyclin D1/2 steady state protein levels were also determined. Steady state protein levels of actin were used to confirm equal loading of protein.

As shown in FIG. 4, GW572016 (lanes 4-6) inhibited p-Erk1/2 and p-AKT steady state protein levels without affecting total steady state protein levels of either molecule. In addition, cyclin D steady state protein levels were inhibited by GW572016. Conversely, trastuzumab (10 mg/kg; lanes 7-9) had little effect on p-Erk1/2, p-AKT, or cyclin D protein expression.

Example 5 p95$^{ErbB2}$ Preferentially Associates with ErbB3

In addition to ErbB2, BT474 cells express EGFR and ErbB3. To determine whether truncated p95$^{ErbB2}$ forms heterodimers, BT474 whole cell extracts were subjected to immunoprecipitation (IP) with either anti-EGFR, anti-ErbB2 or anti-ErbB3 monoclonal antibodies, followed by Western blot using anti-pTyr mAb.

Figure 5:
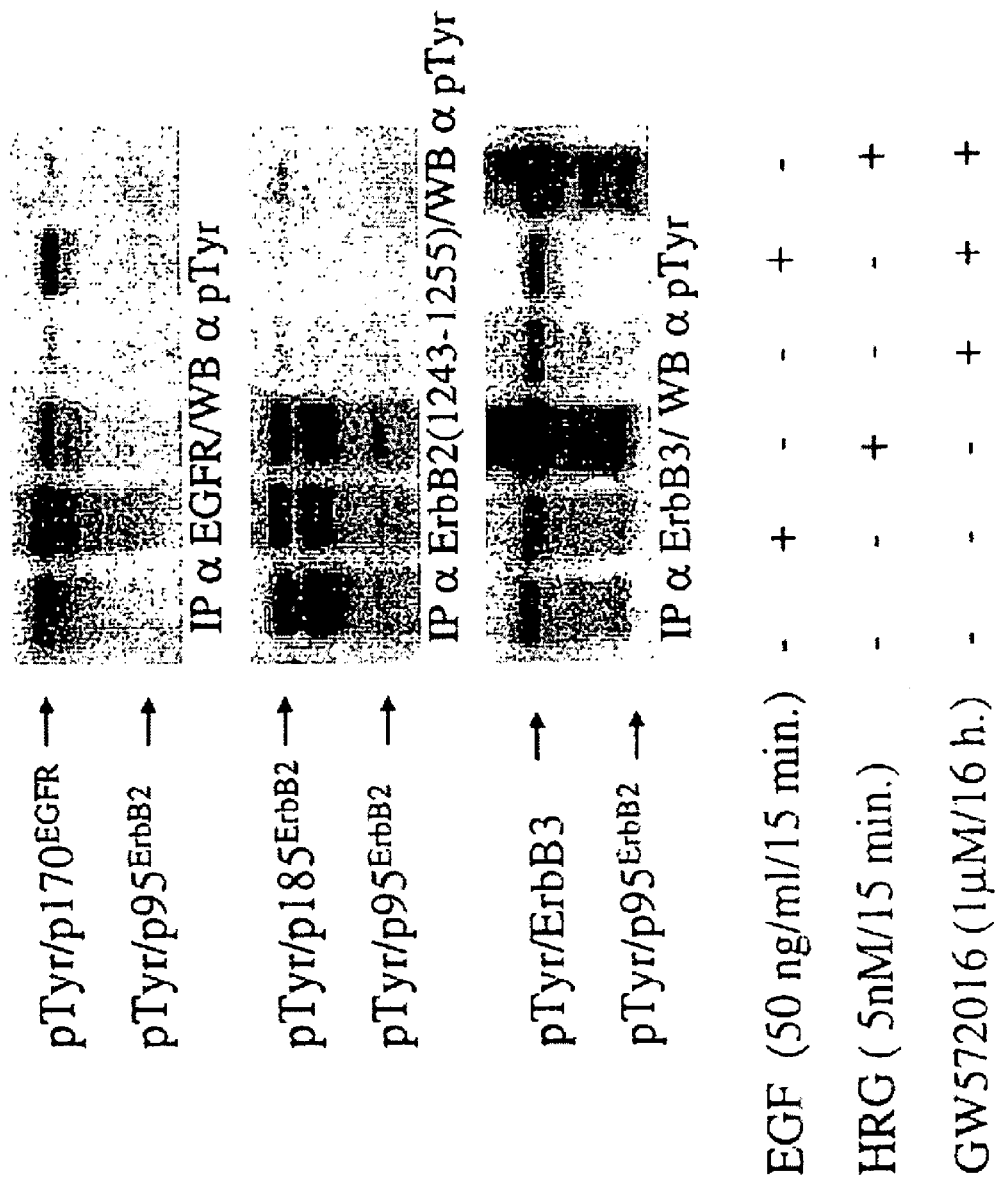
FIG. 5 shows Western Blots indicating the effect of GW572016 on EGF- or Heregulin-induced phosphorylation of $p95^{ErbB2}$, $p170^{EGFR}$, ErbB3, and $p185^{ErbB2}$ in BT474 cells. Cells were cultured in serum-free medium containing 1.5% BSA with (+) or without (−) 1 μM GW572016 for 16 hours and then exposed to EGFR (50 ng/ml) or heregulin (5 nM) for 15 min prior to harvesting. In the uppermost panel of FIG. 5, EGFR immunoprecipitation was followed by Western blot using anti-pTyr monoclonal antibody, and indicated that EGF increased EGFR phosphorylation (compare lanes 1 and 2). GW572016 (1 μM) inhibited baseline phosphorylation of EGFR (compare lanes 1 and 4), and partially blocked EGF induced phosphorylation of EGFR (compare lanes 2 and 5). In contrast, addition of heregulin (HRG) did not exhibit much effect on phosphorylation of EGFR (compare lanes 1 and 3). Moreover, phospho-$p95^{ErbB2}$ did not co-precipitate with EGFR (FIG. 5, upper panel). As shown in the middle panel of FIG. 5, GW572016 inhibited phosphorylation of $p185^{ErbB2}$ and $p95^{ErbB2}$ in both the presence and absence of HRG and EGF (FIG. 5, middle panel). ErbB2 immunoprecipitation was followed by Western blot using anti-pTyr monoclonal antibody. As shown in the lower panel of FIG. 5, HRG, but not EGF, induced ErbB3 and $p95^{ErbB2}$ phosphorylation. GW572016 partially blocked HRG-induced $p95^{ErbB2}$ phosphorylation. Western blot analysis of ErbB3 IP revealed that phospho-$p95^{ErbB2}$ associated with ErbB3.

FIG. 5 demonstrates the effect of GW572016 on EGF- and HRG-induced phosphorylation of p95$^{ErbB2}$ and p185$^{ErbB2}$ in BT474 cells. Cells were cultured in serum-free medium containing 1.5% BSA with or without 1 μMGW572016 for 16 hours and then exposed to EGFR (50 ng/ml) or HRG (5 nM) for 15 minutes prior to harvesting. Phospho-p95$^{ErbB2}$ and p185$^{ErbB2}$ were assessed by IP Western blot using anti-pTyr monoclonal antibody.

As shown in the uppermost panel of FIG. 5, EGFR IP followed by Western blot using anti-pTyr mAb showed that addition of EGF (50 ng/ml) increased EGFR phosphorylation in BT474 cells (compare lanes 1 and 2). GW572016 (1 μM) inhibited baseline phosphorylation of EGFR (compare lanes 1 and 4), and partially blocked EGF induced phosphorylation of EGFR (compare lanes 2 and 5). In contrast, addition of heregulin (HRG) did not exhibit much effect on phosphorylation of EGFR (compare lanes 1 and 3). Moreover, phospho-p95$^{ErbB2}$ did not co-precipitate with EGFR (FIG. 5, upper panel).

As shown in the middle panel of FIG. 5, GW572016 inhibited phosphorylation of p185$^{ErbB2}$ and p95$^{ErbB2}$ in both the presence and absence of HRG and EGF (FIG. 5, middle panel).

As shown in the lower panel of FIG. 5, HRG, but not EGF, induced ErbB3 and p95$^{ErbB2}$ phosphorylation in BT474 cells.

GW572016 partially blocked HRG-induced p95$^{ErbB2}$ phosphorylation. Western blot analysis of ErbB3 IP revealed that phospho-p95$^{ErbB2}$ associated with ErbB3. We were unable to demonstrate ErbB4 in these cells (data not shown).

Figure 6A:
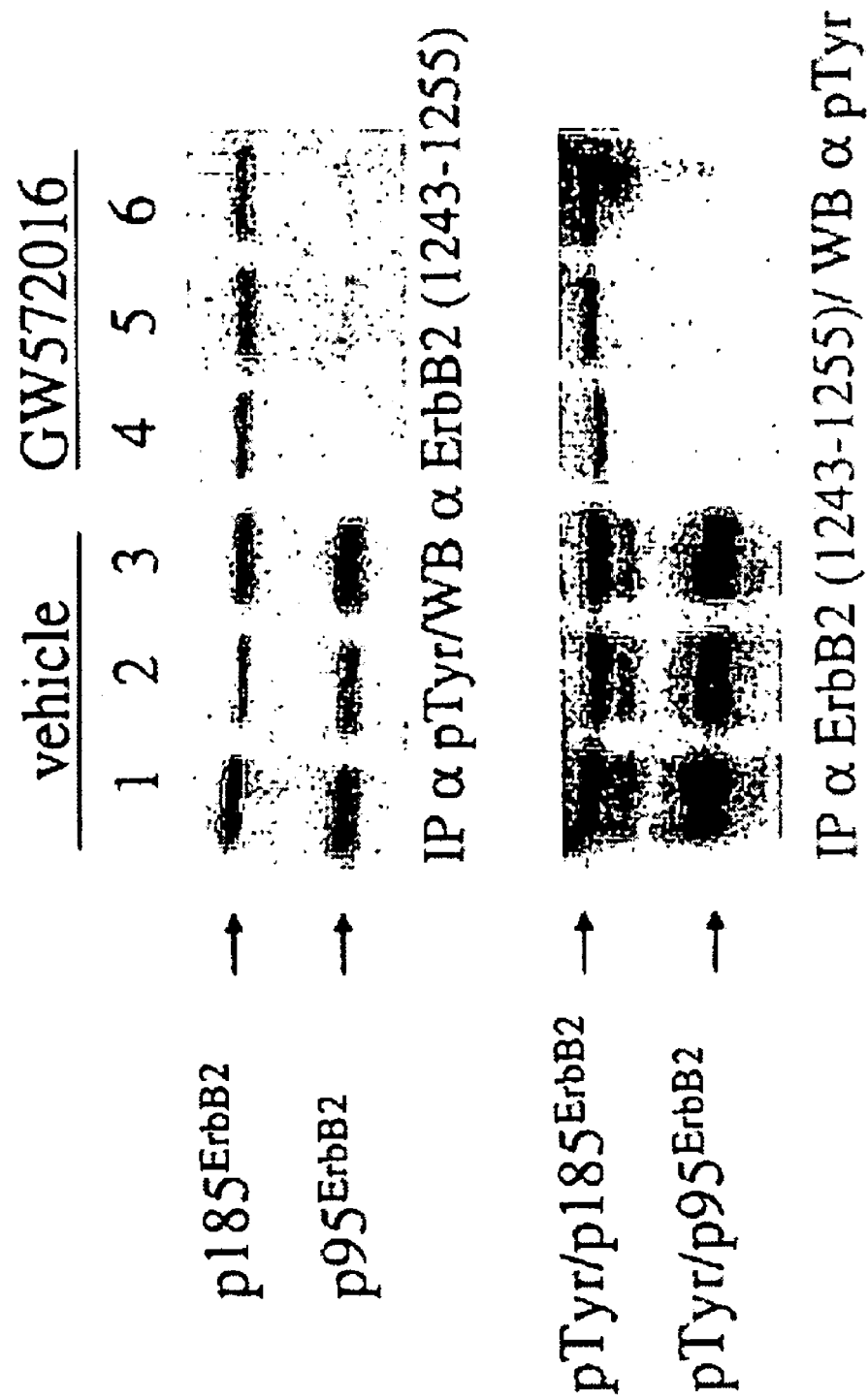
FIG. 6a illustrates the activation-state of $p185^{ErbB2}$ and $p95^{ErbB2}$ in Bt474 tumor xenografts, as assessed by Western blot analysis of anti-pTyr immunoprecipitation probed with anti-ErbB2 monoclonal antibody recognizing the cytoplasmic peptide 1243-1255 (upper panel); and ErbB2 (aa 1243-1255) immunoprecipitation probed with anti-ErbB2 (aa 1243-1255) monoclonal antibody (lower panel). Tumor bearing mice were administered vehicle alone or GW572016, and tumor cell extracts from the animals were compared.
Figure 6B:
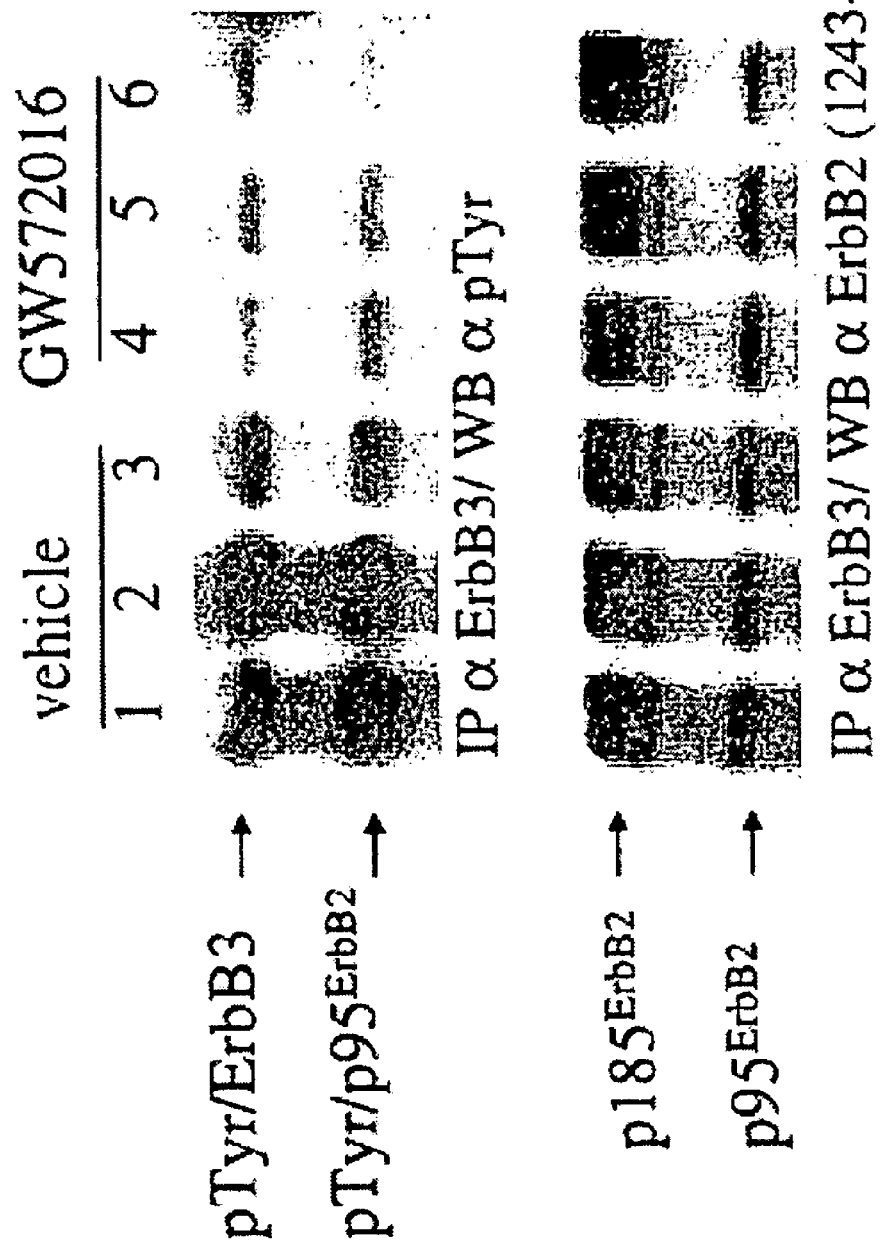
FIG. 6b illustrates the activation-state of ErbB3 and p95$^{ErbB2}$ in Bt474 tumor xenografts, as assessed by Western blot analysis of anti-ErbB3 immunoprecipitation probed with anti-pTyr monoclonal antibody (upper panel); and ErbB2 immunoprecipitation probed with α ErbB2 (aa 1243-1255) Ab (lower panel). Tumor bearing mice were administered vehicle alone or GW572016, and tumor cell extracts from the animals were compared.
Figure 6C:
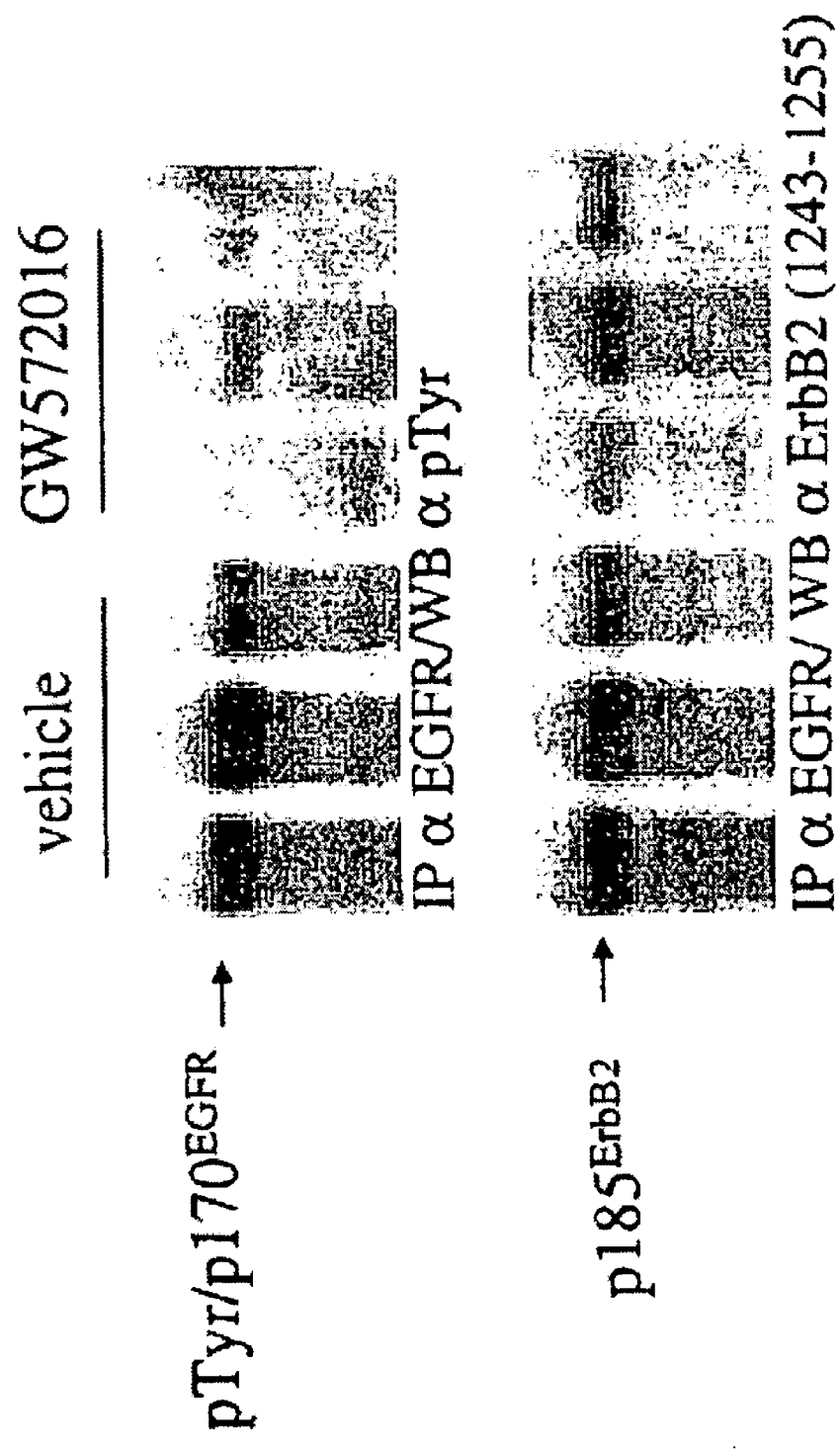
FIG. 6c illustrates the activation state of EGFR in Bt474 tumor xenografts, as assessed by Western blot analysis of an EGFR immunoprecipitate probed with anti-pTyr monoclonal antibody (upper panel); and EGFR immunoprecipitate probed with anti-ErbB2 (aa 1243-1255) monoclonal antibody (lower panel). Tumor bearing mice were administered vehicle alone or GW572016, and tumor cell extracts from the animals were compared.

ErbB3-p95$^{ErbB2}$ heterodimers were also identified in BT474 tumor xenografts by comparing tumor cell extracts from animals treated with vehicle alone or GW572016 (100 mg/kg/dose). Tumor bearing mice were administered vehicle alone or GW572016 (see Example 1, Material and Methods). As shown in FIG. 6a-6c, the activation-state of EGFR, p185$^{ErbB2}$, p95$^{ErbB2}$, and ErbB3 was assessed by IP Western blot. FIG. 6a shows (upper panel) Western blot analysis of anti-pTyr immunoprecipitated proteins probed with anti-ErbB2 mAb recognizing the cytoplasmic peptide 1243-1255, and in the lower panel shows anti-ErbB2 (peptide 1243-1255) immunoprecipitated proteins probed with anti-pTyr mAb. FIG. 6b shows (upper panel) Western blot analysis of anti-ErbB3 immunoprecipitated proteins probed with anti-pTyr mAb; and in the lower panel ErbB3 immunoprecipitated proteins probed with anti-ErbB2 (peptide 1243-1255) Ab. FIG. 6c shows (upper panel) Western blot analysis of EGFR immunoprecipitated proteins probed with anti-pTyr mAb; and in the lower panel EGFR immunoprecipitated proteins probed with anti-ErbB2 (peptide 1243-1255) Ab.

The presence of p95$^{ErbB2}$ in ErbB3 immunoprecipitations was analyzed by Western blot using anti-pTyr or anti-ErbB2 (peptide 1243-1253) Abs. GW572016 treatment markedly inhibited ErbB3 and p95$^{ErbB2}$ tyrosine phosphorylation compared with vehicle treatment alone (FIG. 6a, upper panel). Similar to in vitro studies, ErbB3-p95$^{ErbB2}$ heterodimers were identified in BT474 tumor xenografts (FIG. 6b, upper and lower panels). Whereas p95$^{ErbB2}$ was markedly phosphorylated in vehicle-treated animals, GW572016 inhibited both p95$^{ErbB2}$ and ErbB3 tyrosine phosphorylation (FIG. 6b, upper panel).

In contrast, p95$^{ErbB2}$ did not co-precipitate with EGFR (FIG. 6c, upper and lower panels). Full-length p185$^{ErbB2}$ formed heterodimers with EGFR (lower panel). GW572016, but not vehicle inhibited tyrosine phosphorylation of p95$^{ErbB2}$ and p185$^{ErbB2}$ in tumor xenografts (FIG. 6c).

The cytoplasmic domain of ErbB3 contains at least seven tyrosine residues, which serve as docking sites for the p85 subunit of PI3K (Soltoff et al., 1994; Prigent and Gullick, 1994). Phosphorylation of these tyrosine residues leads to AKT phosphorylation and activation. Since p95$^{ErbB2}$ preferentially associates with ErbB3 in BT474 breast cancer cells, the effects of HRG (an ErbB3 ligand) on MAPK-Erk1/2 and PI3K-AKT were examined. Exponentially growing cells were treated as discussed in Example 1 (Material and methods). GW572016 was added for 24 hours. Equal amounts of protein were analyzed by Western blot for steady state protein levels of total and phosphorylated forms of Erk1/2 and AKT. Proteins were visualized using fluorescent-labeled secondary antibodies and quantified by Odyssey Infrared Imaging System (LI-COR Biosciences, Lincoln, Nebr.).

Figure 7:
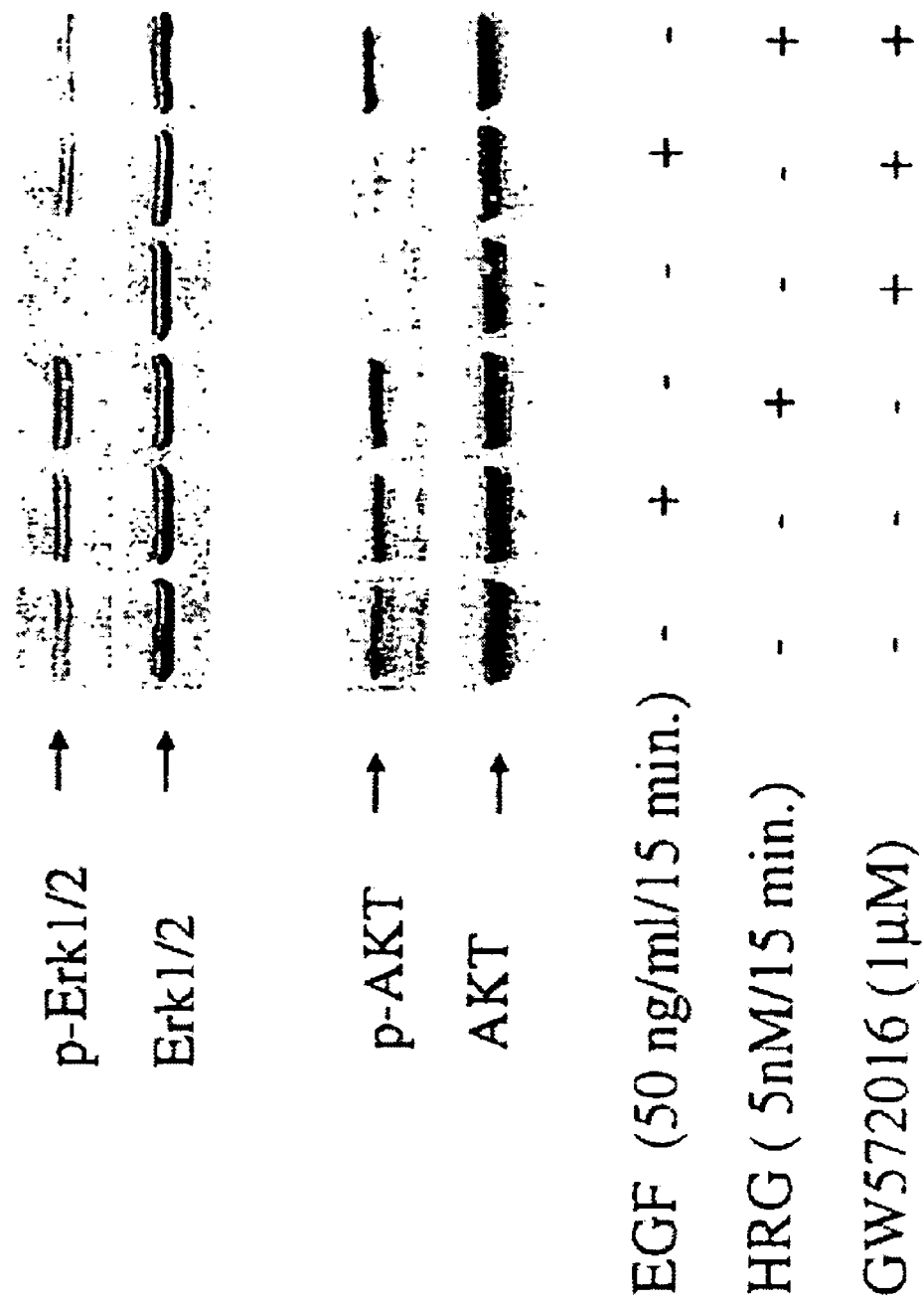
FIG. 7 illustrates that GW572016 inhibits activation of Erk1/2 and AKT by EGF and heregulin in BT474 cells. Addition of GW572016 (1 μM), EGF (50 ng/ml) and Heregulin (5 nM) is indicated by (+). Equal amounts of cellular protein were analyzed by Western blot for steady state protein levels of total and phosphorylated forms of Erk1/2 and AKT. Proteins were visualized using fluorescent-labeled secondary antibodies and quantified by Odyssey Infrared Imaging System.

As shown in FIG. 7, treating BT474 cells with EGF (50 ng/ml) for 15 minutes increased p-Erk1/2 steady state protein levels, which was blocked by GW572016 (1 μM). AKT phosphorylation also increased in response to HRG (5 μM), and was partially inhibited by GW572016 (1 μM). These results indicate that GW572016 inhibits activation of Erk1/2 and AKT by EGF and heregulin, respectively, in BT474 cells.

Example 6

Clinical Use of GW572016 in Trastuzumab Refractory Patients

An open label, multi-dose clinical trial of GW572016 administered to subjects with cancer was carried out to evaluate pharmacokinetic and safety profiles of the compound, and to study the biological effects of the compound on the expression of the activated forms of ErbB2. Patients were randomized to receive one of five different oral doses of GW572016, administered as GW572016 ditosylate salt, in a series of 21 daily doses. Upon completion of the study, patients were able to continue on therapy until disease progression, treatment-emergent toxicities, maximum response, or withdrawal of consent. Male and female subjects with histological confirmation of a solid tumor (non-site specific) that (i) overexpressed total EGFR by IHC or ErbB2 by IHC or FISH; (ii) or expressed activated EGFR or ErbB2, (iii) that could be readily biopsied, and (iv) are amenable to treatment with GW572016, were included in the protocol.

In this clinical trial, of the initial 33 subjects whose responses have been validated, 11 had breast cancer (all previously treated with trastuzumab) with seven of the eleven exhibiting responses (three Partial Responses, four Stable Disease). Additional stable disease was observed in other tumor types including ovarian cancer (2), colorectal cancer (2), lung cancer (1), head and neck cancer (1), adenocarcinoma of unknown primary origin (1), and granular cell cancer (1), providing a total of 15 responses out of 33 subjects (including the seven breast cancer responders).

Thus, several patients in this clinical trial had $p185^{ErbB2}$ overexpressing breast cancer that had previously been treated with trastuzumab. The following summaries are two examples of such patients; detailed results of the each subject in the clinical trial are not provided herein.

Patient No. 372 was a 53 year old female who underwent a mastectomy in January 2001 for estrogen receptor negative, progesterone receptor negative, ErbB2++ breast cancer. Eight of 23 lymph nodes sampled were positive for disease, and there were supraclavicular node metastases and bone metastases. A partial response was seen with paclitaxel/carboplatin/trastuzumab. In February 2002, progressive disease was found and treatment with gemcitabine/trastuzumab was started. In April 2002, progressive disease was found, and treatment with hyperthermia, radiation therapy, and trastuzumab was started. In May 2002, due to progressive disease, treatment with vinorelbine and trastuzumab was started. In August 2002, due to progressive disease, treatment with GW572016 (1200 mg/day) was started. In October 2002, a 70% decrease in two right breast masses was noted, and anterior abdominal wall nodules also improved. Platelets increased from 30,000 to 95,000. However, in December 2002, there was progressive disease noted in the right breast mass upon computerized tomography scan.

Patient No. 361 was a 46-year-old female who underwent a right mastectomy in November 1994 for estrogen receptor negative, progesterone receptor negative, ErbB2+++ breast cancer. Thirteen of 13 lymph nodes sampled were positive for disease. She received adjuvant CAF (cytoxan, adriamycin and 5-fluorouracil) and radiation therapy. In July of 1997, the disease recurred and from fall of 1997 through 1999 she was treated with paclitaxel, doxorubicin, cyclophosphamide/zinecard, 5-fluorouracil, and eniluracil. From January to July 2000 she was treated with trastuzumab, with complete remission of subcutaneous nodules. In November 2000 she began treatment with trastuzumab and vinorelbine, and from July to October 2001 she received paclitaxel. From October 2001 to February 2002 she received trastuzumab and capecitabine. In March 2002 she exhibited subcutaneous nodules and bone metastases, and was started on GW572016 (1200 mg/day). All subcutaneous nodules disappeared within 28 days of starting GW572016; bone metastases did not respond. In June 2002 the subcutaneous nodules returned.

That which is claimed is:

1. A method of selecting therapy for a human subject having a solid epithelial tumor that overexpresses ErbB2, said method comprising:
   (a) determining whether said solid epithelial tumor expresses $p95^{ErbB2}$;
   (b) if said solid epithelial tumor is determined in step (a) to express $p95^{ErbB2}$, selecting a therapy that includes the administration of GW572016 for said human subject.

2. A method according to claim 1 where the expression of $p95^{ErbB2}$ in tumor tissue is determined by immunohistochemical methods.

3. A method according to claim 1 where expression of $p95^{ErbB2}$ is determined by measuring ErbB2 extracellular domain in a sample of the subject's serum.

4. A method according to claim 1 where said tumor is selected from breast, ovarian, colon, head and neck, bladder, renal cell and lung tumors.

5. A method according to claim 4 where said solid epithelial tumor is a breast tumor.

6. A method according to claim 1 where said subject has previously been treated with trastuzumab.

7. A method of selecting therapy for a human subject having a solid epithelial tumor that overexpresses ErbB2, said method comprising:
   (a) measuring the serum level of ErbB2 ECD of the subject to determine if said ECD level is elevated;
   (b) selecting a therapy that includes the administration of GW572016 for said human subject if said ECD level is elevated.

8. A method of selecting therapy for a human subject having a solid epithelial tumor that overexpresses ErbB2, said method comprising:
   (a) measuring $p95^{ErbB2}$ levels is samples of said solid epithelial tumor to determine if $p95^{ErbB2}$ overexpressed;
   (b) selecting a therapy that includes the administration of GW572016 for said human subject if $p95^{ErbB2}$ is overexpressed.

* * * * *